(12) United States Patent
Eon-Duval et al.

(10) Patent No.: US 8,168,185 B2
(45) Date of Patent: May 1, 2012

(54) PROCESS FOR THE PURIFICATION OF ANTI CD-25 ANTIBODIES

(75) Inventors: Alex Eon-Duval, Vevy (CH); Celine Teppet, St. Pierre d'Entremont (FR)

(73) Assignee: Merck Serono SA, Coinsins, Vaud (CH)

( * ) Notice: Subject to any disclaimer, the term of this patent is extended or adjusted under 35 U.S.C. 154(b) by 0 days.

(21) Appl. No.: 12/521,789

(22) PCT Filed: Jan. 17, 2008

(86) PCT No.: PCT/EP2008/050501
§ 371 (c)(1),
(2), (4) Date: Jun. 30, 2009

(87) PCT Pub. No.: WO2008/087184
PCT Pub. Date: Jul. 24, 2008

(65) Prior Publication Data
US 2010/0022757 A1 Jan. 28, 2010

Related U.S. Application Data

(60) Provisional application No. 60/886,376, filed on Jan. 24, 2007.

(30) Foreign Application Priority Data

Jan. 17, 2007 (EP) ..................................... 07000859

(51) Int. Cl.
*C07K 1/00* (2006.01)
(52) U.S. Cl. ................. 424/133.1; 530/387.1; 530/387.3
(58) Field of Classification Search ............... 424/133.1; 530/387.1, 387.3
See application file for complete search history.

(56) References Cited

FOREIGN PATENT DOCUMENTS
EP 1614693 11/2006
WO WO 2005/100394 10/2005

OTHER PUBLICATIONS

EMD Chemicals, Inc., Fractogel Chromatograpgy Brochure (pp. 1-8; Nov. 2, 2010).*
MacCallum et al. (J. Mol. Biol. (1996) 262:732-745)).*
Casset et al. (BBRC 307, 198-205, (2003)).*
Holm et al. (Mol. Immunol. 44: 1075-1084 (2007)).*
Chen et al. (J. Mol. Bio. 293, 865-881 (1999)).*
Dufner (Trends Biotechnol. 24(11):523-29 (2006)).*
Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Armour, K. L. et al. "Recombinant Human IgG Molecule Lacking Fcγ Receptor I Binding and Monocyte Triggering Activities" *Eur J Immunol.*, 1999, pp. 2613-2624, vol. 29, No. 8.
Carter, P. J. "Potent Antibody Therapeutics by Design" *Nat Rev Immunol.*, May 2006, pp. 343-357, vol. 6, No. 5.
Follman, D. K. et al. "Factorial Screening of Antibody Purification Processes Using Three Chromatography Steps Without Protein A" *J Chromatogr A*, 2004, pp. 79-85, vol. 1024, No. 1-2.
Graf, H. et al. "Ion Exchange Resins for the Purification of Monoclonal Antibodies from Animal Cell Culture" *Bioseperation*, 1994, pp. 7-20, vol. 4.
Grantham, R. "Amino Acid Difference Formula to Help Explain Protein Evolution" *Science*, 1974, pp. 862-864, vol. 185.
Hinton, P. R. et al. "Engineered Human IgG Antibodies with Longer Serum Half-Lives in Primates" *J Biol Chem.*, Feb. 20, 2004, pp. 6213-6216, vol. 279, No. 8.
Idusogie, E. E. et al. "Mapping of the C1q Binding Site on Rituxan, a Chimeric Antibody with a Human IgG1 Fc" *J Immunol.*, 2000, pp. 4178-4184, vol. 164, No. 8.
Idusogie, E. E. et al. "Engineered Antibodies with Increased Activity to Recruit Complement" *J Immunol.*, 2001, pp. 2571-2575, vol. 166, No. 4.
Ishihari, T. et al. "Optimization of Monoclonal Antibody Purification by Ion-Exchange Chromatography: Application of Simple Methods with Linear Gradient Elution Experimental Data" *J Chromatogr A.*, 2005, pp. 99-106, vol. 1069.
Ishihari, T. et al. "Rational Methods for Predicting Human Monoclonal Antibodies Retention in Protein A Affinity Chromatography and Cation Exchange Chromatography: Structure-Based Chromatography Design for Monoclonal Antibodies" *J Chromatogr A.*, 2005, pp. 126-138, vol. 1093.
Shields, R. L. et al. "High Resolution Mapping of the Binding Site on Human IgG1 for FcγRI, FcγRII, FcγRIII, and FcRn and Design of IgG1 Variants with Improved Binding to the FcγR" *J Biol Chem.*, Mar. 2, 2001, pp. 6591-6604, vol. 276, No. 9.
Steurer, W. et al. "Ex Vivo Coating of Islet Cell Allografts with Murine CTLA4/Fc Promotes Graft Tolerance" *J Immunol.*, 1995, pp. 1165-1174, vol. 155, No. 3.
Vaccaro, C. et al. "Engineering the Fc Region of Immunoglobulin G to Modulate in vivo Antibody Levels" *Nat Biotechnol.*, 2005, vol. 1283-1288, vol. 23, No. 10.
Written Opinion in International Application No. PCT/EP2008/050501, Jul. 2, 2008, pp. 1-7.
Desilva, F. J. "Essentials of Ion Exchange" Mar. 17, 1999, pp. 1-5, Presented at the 25th Annual WQA Conference.
"Ion Exchange Chromatography & Chromatofocusing; Principles and Methods" *Amersham Biosciences*, 2004, pp. 1-188, Edition AA.
"Ion Exchange Resins: Classification and Properties" *Polymer Products from Aldrich*, pp. 28-30, http://www.sigmaaldrich.com/etc/medialib/docs/Aldrich/Instructions/ion_exchange_resins.Par.0001.File.tmp/ion_exchange_resins.pdf, accessed on Apr. 14, 2011.

* cited by examiner

*Primary Examiner* — Lynn Bristol
(74) *Attorney, Agent, or Firm* — Saliwanchik, Lloyd & Eisenschenk

(57) ABSTRACT

The invention relates to a process for the purification of an Fc-containing protein based on cation exchange chromatography.

30 Claims, 4 Drawing Sheets

PROCESS FOR THE PURIFICATION OF ANTI CD-25 ANTIBODIES

CROSS-REFERENCE TO RELATED APPLICATION

This application is the U.S. national stage application of International Patent Application No. PCT/EP2008/050501, filed Jan. 17, 2008, which claims the benefit of U.S. Provisional Patent Application No. 60/886,376, filed Jan. 24, 2007, the disclosures of which are hereby incorporated by reference in their entireties, including all figures, tables and amino acid or nucleic acid sequences.

FIELD OF THE INVENTION

The present invention is in the field of protein purification. More specifically, it relates to the purification of Fc-containing proteins. The method comprises at least a step of purification via cation exchange chromatography.

BACKGROUND OF THE INVENTION

Proteins have become commercially important as drugs that are generally called "biologicals". One of the greatest challenges is the development of cost effective and efficient processes for purification of proteins on a commercial scale. While many methods are now available for large-scale preparation of proteins, crude products, such as cell culture supernatants, contain not only the desired product but also impurities, which are difficult to separate from the desired product. Although cell culture supernatants of cells expressing recombinant protein products may contain less impurities if the cells are grown in serum-free medium, the host cell proteins (HCPs) still remain to be eliminated during the purification process. Additionally, the health authorities request high standards of purity for proteins intended for human administration.

A number of chromatographic systems are known that are widely used for protein purification.

Ion exchange chromatography systems are used for separation of proteins primarily on the basis of differences in charge.

Anion exchangers can be classified as either weak or strong. The charge group on a weak anion exchanger is a weak base, which becomes de-protonated and, therefore, loses its charge at high pH. DEAE-sepharose is an example of a weak anion exchanger, where the amino group can be positively charged below pH ~9 and gradually loses its charge at higher pH values. Diethylaminoethyl (DEAE) or diethyl-(2-hydroxy-propyl)aminoethyl (QAE) have chloride as counter ion, for instance. A strong anion exchanger, on the other hand, contains a strong base, which remains positively charged throughout the pH range normally used for ion exchange chromatography (pH 1-14). Q-sepharose (Q stands for quaternary ammonium) is an example for a strong anion exchanger.

Cation exchangers can also be classified as either weak or strong. A strong cation exchanger contains a strong acid (such as a sulfopropyl group) that remains charged from pH 1-14; whereas a weak cation exchanger contains a weak acid (such as a carboxymethyl group), which gradually loses its charge as the pH decreases below 4 or 5. Carboxymethyl (CM) and sulphopropyl (SP) have sodium as counter ion, for example.

Hydrophobic interaction chromatography (HIC) is used to separate proteins on the basis of hydrophobic interactions between the hydrophobic moieties of the protein and insoluble, immobilized hydrophobic groups on the matrix. Generally, the protein preparation in a high salt buffer is loaded on the HIC column. The salt in the buffer interacts with water molecules to reduce the salvation of the proteins in solution, thereby exposing hydrophobic regions in the protein which are then adsorbed by hydrophobic groups on the matrix. The more hydrophobic the molecule, the less salt is needed to promote binding. Usually, a decreasing salt gradient is used to elute proteins from a column. As the ionic strength decreases, the exposure of the hydrophilic regions of the protein increases and proteins elute from the column in order of increasing hydrophobicity.

Hydrophobic charge induction chromatography (HCIC) is another mode of chromatography based on the pH dependent behavior of heterocyclic ligands that ionize at low pHs. While adsorption on this mode of chromatography occurs via hydrophobic interactions, desorption is facilitated by lowering the pH to produce charge repulsion between the ionizable ligand and the bound protein (e.g. sorbent MEP Hypercel from Biosepra).

Yet a further way of purifying proteins is based on the affinity of a protein of interest to another protein that is immobilized to a chromatography resin. Examples for such immobilized ligands are the bacterial cell wall proteins Protein A and Protein G, having specificity to the Fc portion of certain immunoglobulins. Although both Protein A and Protein G have a strong affinity for IgG antibodies, they have varying affinities to other immunoglobulin classes and isotypes as well.

Affinity chromatography on protein A allows the clearance of more than 99.5% of the impurities such as host cell proteins (HCPs), DNA, viruses, incomplete forms of the antibodies in only one step. However, the major disadvantage of this purification technique is the cost of the resin. It is approximately 30 times more expensive than ion exchange resins and can represent nearly 35% of the total cost of the raw material used for large scale purification. Protein A resin also presents some stability problems as Protein A residues, which are potentially immunogenic, are found in the eluate and need therefore to be cleared. Protein A resin is also difficult to sanitize as the ligand is easily denatured by common sanitization solutions like sodium hydroxide and this represents a major problem in production in the event of contamination as re-use of the resin may be detrimentally affected.

Combinatorial chemistry has enabled the synthesis of a wide variety of ligands which can mimic the action of protein A e.g. the triazine derivatives that mimic the Phe-132, Tyr-133 dipeptide binding site in the hydrophobic core structure of Protein A (marketed as MAbsorbent A1P, A2P, and A3P by Prometic).

A further way of purifying antibodies uses affinity ligands developed by making use of Camelidae heavy chain antibody fragments (CAPTURESELECT products from The Bio Affinity Company).

In the field of antibody purification, Follman and Fahrner (2004) have determined that the same host cell protein removal obtained with a process incorporating Protein A chromatography can be achieved using a process with no affinity chromatography steps. They identified three non-affinity purification processes including hydrophobic interaction chromatography, anion-exchange chromatography and cation-exchange chromatography that remove CHOPs (Chinese Hamster Ovary Cell Proteins) to levels comparable to the traditional Protein A process (J Chromatogr A. 2004. Jan. 23; 1024(1-2):79-85); WO 03/102132A2). They also disclose a method for protein purification that involves the combination of non-affinity chromatography and high performance tangential flow filtration (HPTFF). After a first purification (capture) step on cation exchange chromatography the host cell protein content was about 14,000 ppm.

Antibodies, or immunoglobulins (Igs) consist of light chains and heavy chains linked together by disulphide bonds. The first domain located at the amino terminus of each chain is variable in amino acid sequence, providing the vast spectrum of antibody binding specificities. These domains are known as variable heavy (VH) and variable light (VL) regions. The other domains of each chain are relatively invariant in amino acid sequence and are known as constant heavy (CH) and constant light (CL) regions.

The major classes of antibodies are IgA, IgD, IgE, IgG and IgM; and these classes may be further divided into subclasses (isotypes). For example, the IgG class has four subclasses, namely, $IgG_1$, $IgG_2$, $IgG_3$, and $IgG_4$.

The differences between antibody classes are derived from differences in the heavy chain constant regions, containing between 1 and 4 constant domains (CH1-CH4), depending on the immunoglobulin class. A so-called hinge region is located between the CH1 and CH2 domains. The hinge region is particularly sensitive to proteolytic cleavage; such proteolysis yields two or three fragments depending on the precise site of cleavage. The part of the heavy chain constant region containing the CH2 and CH3 domains, optionally together with the hinge region, is also called the "Fc" part of the immunoglobulin. Antibodies are thus Fc-containing proteins.

Several antibodies that are used as therapeutic proteins are known. Examples for recombinant antibodies on the market are for instance: Abciximab, Rituximab, Basiliximab, Daclizumab, Palivizumab, Infliximab, Trastuzumab, Alemtuzumab, Adalimumab, Cetuximab, Efalizumab, Ibritumomab, Bevacizumab, or Omalizumab.

Another type of Fc-containing proteins are the so-called Fc-fusion proteins. Fc-fusion proteins are chimeric proteins consisting of the effector region of a protein, such as the Fab region of an antibody or the binding region of a receptor, fused to the Fc region of an immunoglobulin that is frequently an immunoglobulin G (IgG). Fc-fusion proteins are widely used as therapeutics as they offer advantages conferred by the Fc region, such as:

The possibility of purification using protein A or protein G affinity chromatography with affinities which vary according to the IgG isotype. Human $IgG_1$, $IgG_2$ and $IgG_4$ bind strongly to Protein A and all human IgGs including $IgG_3$ bind strongly to Protein G;

An increased half-life in the circulatory system, since the Fc region binds to the salvage receptor FcRn which protects from lysosomal degradation;

Depending on the medical use of the Fc-fusion protein, the Fc effector functions may be desirable. Such effector functions include antibody-dependent cellular cytotoxicity (ADCC) through interactions with Fc receptors (FcγRs) and complement-dependent cytotoxicity (CDC) by binding to the complement component 1q (C1q). IgG isoforms exert different levels of effector functions. Human $IgG_1$ and $IgG_3$ have strong ADCC and CDC effects while human $IgG_2$ exerts weak ADCC and CDC effects. Human $IgG_4$ displays weak ADCC and no CDC effects.

Serum half-life and effector functions can be modulated by engineering the Fc region to increase or reduce its binding to FcRn, FcγRs and C1q respectively, depending on the therapeutic use intended for the Fc-fusion protein.

In ADCC, the Fc region of an antibody binds to Fc receptors (FcγRs) on the surface of immune effector cells such as natural killers and macrophages, leading to the phagocytosis or lysis of the targeted cells.

In CDC, the antibodies kill the targeted cells by triggering the complement cascade at the cell surface. IgG isoforms exert different levels of effector functions increasing in the order of $IgG_4 < IgG_2 < IgG_1 = IgG_3$. Human $IgG_1$ displays high ADCC and CDC, and is the most suitable for therapeutic use against pathogens and cancer cells.

Under certain circumstances, for example when depletion of the target cell is undesirable, abrogating effector functions is required. On the contrary, in the case of antibodies intended for oncology use, increasing effector functions may improve their therapeutic activity (Carter et al., 2006)

Modifying effector functions can thus be achieved by engineering the Fc region to either improve or reduce binding of FcγRs or the complement factors.

The binding of IgG to the activating (FcγRI, FcγRIIa, FcγRIIIa and FcγRIIIb) and inhibitory (FcγRIIb) FcγRs or the first component of complement (C1q) depends on residues located in the hinge region and the CH2 domain. Two regions of the CH2 domain are critical for FcγRs and complement C1q binding, and have unique sequences in $IgG_2$ and $IgG_4$. For instance, substitution of $IgG_2$ residues at positions 233-236 into human $IgG_1$ greatly reduced ADCC and CDC (Armour et al., 1999 and Shields et al., 2001).

Numerous mutations have been made in the CH2 domain of IgG and their effect on ADCC and CDC was tested in vitro (Shields et al., 2001, Idusogie et al., 2001 and 2000, Steurer et al., 1995). In particular, a mutation to alanine at E333 was reported to increase both ADCC and CDC (Idusogie et al., 2001 and 2000).

Increasing the serum half-life of a therapeutic antibody is another way to improve its efficacy, allowing higher circulating levels, less frequent administration and reduced doses. This can be achieved by enhancing the binding of the Fc region to neonatal FcR (FcRn). FcRn, which is expressed on the surface of endothelial cells, binds the IgG in a pH-dependent manner and protects it from degradation. Several mutations located at the interface between the CH2 and CH3 domains have been shown to increase the half-life of $IgG_1$ (Hinton et al., 2004 and Vaccaro et al., 2005).

The following Table 1 summarizes some known mutations of the IgG Fc-region (taken from Invivogen's website).

| Engineered Fc | IgG Isotype | Mutations | Properties | Potential Benefits | Applications |
| --- | --- | --- | --- | --- | --- |
| hIgG1e1 | human IgG1 | T250Q/M428L | Increased plasma half-life | Improved localization to target; increased efficacy; reduced dose or frequency of administration | Vaccination; therapeutic use |
| hIgG1e2 | human IgG1 | M252Y/S254T/T256E + H433K/N434F | Increased plasma half-life | Improved localization to target; increased efficacy; reduced dose or frequency of administration | Vaccination; therapeutic us |

-continued

| Engineered Fc | IgG Isotype | Mutations | Properties | Potential Benefits | Applications |
|---|---|---|---|---|---|
| hIgG1e3 | human IgG1 | E233P/L234V/L235A/ ?G236 + A327G/A3305/P331S | Reduced ADCC and CDC | Reduced adverse events | Therapeutic use without cell depletion |
| hIgG1e4 | human IgG1 | E333A | Increased ADCC and CDC | Increased efficacy | Therapeutic use with cell depletion |
| hIgG2e1 | human IgG2 | K322A | Reduced CDC | Reduced adverse events | Vaccination; therapeutic use |

Given the therapeutic utility of Fc-containing proteins, particularly antibodies and Fc-fusion proteins, there is a need for significant amounts of highly purified protein that is adequate for human administration. Effective purification processes are suitable for large-scale purification of Fc-containing proteins.

SUMMARY OF THE INVENTION

The present invention is based on the development of a cation exchange chromatography step for the purification of Fc-containing proteins.

Therefore, in a first aspect, the invention relates to a method for separating and purifying an Fc-containing protein from a fluid, comprising at least a cation exchange chromatography purification step comprising the steps of:
  a. Binding the Fc-containing protein to a cation exchange resin;
  b. Washing the cation exchange resin with a buffer at a pH about 1 unit below the isoelectric point of the Fc-containing protein, the buffer having a conductivity of about 2 to 6 mS/cm; and
  c. Eluting the Fc-containing protein with a buffer at a pH about 1 unit below the isoelectric point of the Fc-containing protein with an increasing salt gradient.

According to the method of the invention, the eluate of the cation exchange chromatography step can be subjected to one or more further purification steps selected from anion exchange chromatography and hydrophobic interaction chromatography.

This process is preferably used for purifying Fc-containing proteins selected from antibodies and Fc-fusion proteins.

It has been surprisingly shown that the HCP level in the eluate of the cation exchange chromatography step was less than 10,000 ppm or of less than 5,000 ppm and the level of the aggregates level was reduced to less than 1%.

It has further been shown that the wash step (b) allowed removal of incomplete Fc-containing protein fragments such as e.g. incomplete antibody fragments consisting of free heavy chains or free light chains. Therefore the second aspect of the invention relates to the use of a cation exchange chromatography for capturing an Fc-containing protein from a fluid, preferably clarified cell culture supernatant, wherein, following binding of the Fc-containing protein to the cation exchange resin, the resin is washed with a buffer at a pH of about 1 unit below the isoelectric point of the Fc-containing protein.

BRIEF DESCRIPTION OF THE SEQUENCE LISTING

Figure 1:
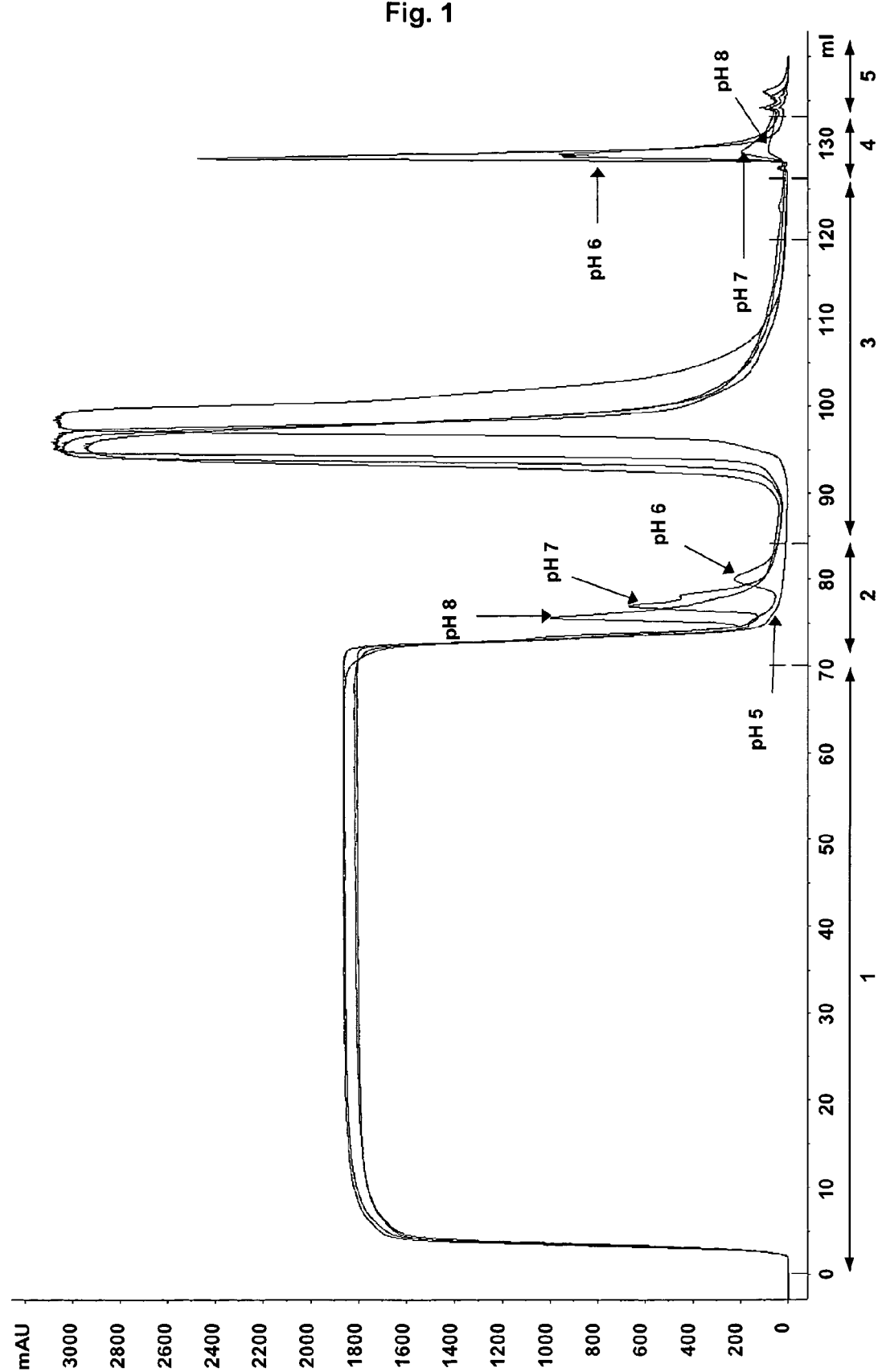
FIG. 1: shows the chromatographic profile of the cation exchange chromatography described in Example 1. 1—Load, 2—Wash, 3—Elution in a NaCl gradient, 4—Regeneration/Sanitisation, 5—Re-equilibration.
Elution at pH 5: NaCl gradient from 0 to 1 M, pH 6: NaCl gradient from 0 to 0.8 M, pH 7: NaCl gradient from 0 to 0.6 M, pH 8: NaCl gradient from 0 to 0.45 M.

SEQ ID NO 1: Anti-CD25 rhAb light chain variable region (VH).
SEQ ID NO 2: Anti-CD25 rhAb heavy chain variable region (VL).
SEQ ID NO 3: CDR1 of anti-CD25 rhAb heavy chain variable region.
SEQ ID NO 4: CDR2 of anti-CD25 rhAb heavy chain variable region.
SEQ ID NO 5: CDR3 anti-CD25 rhAb heavy chain variable region.
SEQ ID NO 6: CDR1 of the anti-CD25 rhAb light chain variable region.
SEQ ID NO 7: CDR2 of the anti-CD25 rhAb light chain variable region.
SEQ ID NO 8: CDR3 of the anti-CD25 rhAb light chain variable region.

DETAILED DESCRIPTION OF THE INVENTION

The present invention is based on the development of a purification method based on a cation exchange chromatography step that can significantly reduce the amount or extent of impurities such as incomplete Fc-containing protein fragments, aggregates and host cell proteins (HCPs) that may be present in a fluid or composition of an Fc-containing protein.

The invention therefore relates to a method for separating and purifying an Fc-containing protein from a fluid, comprising at least a cation exchange chromatography step comprising the steps of:
  a. Binding the Fc-containing protein to a cation exchange resin;
  b. Washing the cation exchange resin with a buffer at a pH about 1 unit below the isoelectric point of the Fc-containing protein, the buffer having a conductivity of about 2 to 6 mS/cm; and
  c. Eluting the Fc-containing protein with a with a buffer at a pH about 1 unit below the isoelectric point of the Fc-containing protein with an increasing salt gradient.

This purification step will be referred to herein as cation exchange chromatography step (CEX).

The fluid comprising the Fc-containing protein may be any composition or preparation, such as e.g. a body fluid derived from a human or animal, or a fluid derived from a cell culture, such as e.g. a cell culture supernatant or cell culture harvest. Preferably it is clarified cell culture harvest. It may also be a fluid derived from another purification step, such as e.g. the eluate or flow-through from a capture step or any other suitable purification step preceding the cation exchange chromatography step.

In accordance with the present invention, a fluid comprising an Fc-containing protein is first subjected to cation-exchange chromatography. The fluid may preferably be cell culture material, e.g. solubilised cells, more preferably cell culture supernatant. The term "cell culture supernatant", as used herein, refers to a medium in which cells are cultured and into which proteins are secreted provided they contain appropriate cellular signals, so-called signal peptides. It is preferred that the Fc-containing protein expressing cells are cultured under serum-free culture conditions. Thus, preferably, the cell culture supernatant is devoid of animal-serum derived components. Most preferably, the cell culture medium is chemically defined medium.

Preferably, the protein purified according to the invention is a Fc-containing protein such as, e.g. an antibody, more preferably a human, humanized or chimeric antibody comprising human constant regions, preferably an IgG1 antibody, it can also preferably be an Fc-fusion protein. Fc-containing proteins are chimeric proteins consisting of the effector region of a protein, such as e.g. the Fab region of an antibody or the binding region of a receptor, fused to the Fc region of an immunoglobulin that is frequently an immunoglobulin G (IgG).

The cation exchange chromatography according to the method of the present invention may be used in a purification method having one or more additional steps. The additional steps may precede or follow the cation exchange chromatography step. Preferably they follow the cation exchange chromatography step. More preferably, they are selected from, anion exchange chromatography (AEX) and hydrophobic interaction chromatography (HIC).

Therefore in a preferred embodiment, the eluate of the purification step on cation exchange chromatography is subjected to a further purification step selected from anion exchange chromatography or hydrophobic interaction chromatography.

In a further preferred embodiment, the method according to the invention comprises, further to the cation exchange chromatography step, two purification steps on anion exchange chromatography and hydrophobic interaction chromatography, in either order.

The flow-through of the anion exchange chromatography is preferably collected. Hence, the method of the invention may comprise cation exchange chromatography, anion exchange chromatography and hydrophobic interaction chromatography or cation exchange chromatography, hydrophobic interaction chromatography and anion exchange chromatography steps. One or more further purification steps may precede or follow the method of the invention, if required.

Before loading the fluid comprising an Fc-containing protein on the cation-exchange chromatography, the fluid is preferably either adjusted to a pH of less than 5, preferably about 4 or as an alternative diluted with water to a conductivity of less than about 4 mS/cm at about pH7. This is essential to allow binding of the Fc-containing protein to the cation-exchange resin.

The pH of less than 5 may e.g. be at about 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1 or at about 2.0.

The conductivity of less than 4 mS/cm can be e.g. 4.0, 4.9, 4.8, 4.7, 4.6, 4.5, 4.4, 4.3, 4.2, 4.1, 3.0, 2.9, 2.8, 2.7, 2.6, 2.5, 2.4, 2.3, 2.2, 2.1, 2.0 or 1.9 mS/cm. It is preferably at about 2.8 mS/cm.

Adjustment of pH to about 4 is preferred since it is easily performed by addition of concentrated acetic acid without increasing the load volume significantly. In addition, dynamic capacity is high when using Fractogel SE Hicap as the cation-exchange resin (40 to 50 g of human IgG1 per liter of packed resin).

In step (b) of the cation exchange chromatography according to the invention, the cation exchange resin is washed with a buffer having a conductivity of about 2 to about 6 mS/cm and at a pH about one pH unit below the isoelectric point of the Fc-containing protein.

The buffer in step (b) may e.g. have a conductivity of about 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9 or 6 mS/cm.

In a further preferred embodiment, the cation exchange column is washed in step (b) with a buffer at a pH ranging from about 7 to about 8.5 at a conductivity of about 2 to 6 mS/cm. The pH may e.g. be at about 7.0, 7.05, 7.1, 7.15, 7.2, 7.25, 7.3, 7.35, 7.4, 7.45, 7.5, 7.55, 7.6, 7.65, 7.7, 7.75, 7.8, 7.85, 7.9, 7.95, 8, 8.05, 8.1, 8.15, 8.2, 8.25, 8.3, 8.35, 8.4, 8.45 or about 8.5.

In a most preferred embodiment, the cation exchange resin in step (b) is washed with a phosphate buffer at about pH 8, having a conductivity of about 3.5 mS/cm.

In a further preferred embodiment, the washing step is carried out in a buffer comprising about 10 to about 30, preferably 20 mM sodium phosphate. The buffer may e.g. comprise 10, 11, 12, 13, 14, 15, 16, 17, 18, 19, 20, 21, 22, 23, 24, 25, 26, 27, 28, 29 or 30 mM sodium phosphate.

In step (c) of the cation exchange chromatography according to the invention, the Fc-containing protein is eluted from the cation exchange resin at a pH about 1 unit below the isoelectric point of the Fc-containing protein with an increasing salt gradient.

The elution of the Fc-containing protein may be carried out using any suitable salt e.g. NaCl or KCl. As increasing NaCl salt gradient is preferred.

The increasing salt gradient according to the method of the invention is preferably a shallow gradient.

Preferably, the Fc-containing protein is eluted from the cation exchange resin with an increasing salt gradient at a conductivity ranging from about 2 to about 15 mS/cm at a pH of about 7 to about 8.5. The conductivity gradient ranging from about 2 to about 15 mS/cm may be generated by an increase in sodium chloride concentration from 0 mM to about 150 mM. The pH is maintained constant during the gradient and may be between 7.0 and 8.5.

In a preferred embodiment, the Fc-containing protein is eluted from the cation exchange resin at pH ranging from about 7.0 to about 8.5 with an increasing salt gradient buffer ranging from about 0 to about 150 mM NaCl. The increasing salt gradient buffer can e.g. range from about 0 to about 155, 0 to 145, 5 to 145, 5 to 150, 5 to 155, 10 to 145, 10 to 150 or about 10 to about 155 mM NaCl.

The pH of the elution buffer can be at about 7.0, 7.1, 7.15, 7.2, 7.25, 7.3, 7.35, 7.4, 7.45, 7.5, 7.55, 7.6, 7.65, 7.7, 7.75, 7.8, 7.85, 7.9, 7.95, 8, 8.05, 8.1, 8.15, 8.2, 8.25, 8.3, 8.35, 8.4, 8.45, or about 8.5.

In a further preferred embodiment, the Fc-containing protein in step (c) is eluted from the cation exchange resin with a gradient of conductivity at a pH of about one pH unit below the isoelectric point of the Fc-containing protein.

Elution of Fc-containing protein is monitored by the absorbance at 280 nm and fractions are collected during the descending phase of the peak of absorbance. Fractions are then pooled so as to avoid aggregates and HCPs in the tail of the peak of elution, this is referred herein as "cutting out of the tail". The tail of the peak of elution may present a distinct shoulder which may preferably be removed from the main peak. Alternatively, an isocratic elution can be performed with buffer at a conductivity and pH that will prevent the elution of aggregates and HCPs. Preferably, the Fc-containing protein is eluted in a buffer with an increasing NaCl gradient from about 0 to about 150 mM of NaCl at about pH 8.

In a further preferred embodiment, the elution in step (c) is carried out in a buffer selected from sodium phosphate, Tris or HEPES.

In a preferred embodiment of the invention, cutting out the tail of the elution peak is performed in step (c) of the cation exchange chromatography step.

The cation exchange chromatography may be carried out on any suitable cation exchange resin, such as e.g. weak or strong cation exchangers as explained above in the Background of the Invention.

Preferably, the cation exchange resin used in the cation exchange chromatography is a strong cation exchange resin. A column commercially available under the name Fractogel EMD SE Hicap (M) (from Merck) is an example of a cation exchange resin that is particularly suitable in the context of the present method.

In a preferred embodiment, the cation exchange resin is loaded with clarified cell culture supernatant adjusted to pH 4 by addition of concentrated acetic acid and after removal of precipitated material by centrifugation or filtration. In another embodiment, the cation exchange resin is loaded with cell culture material adjusted to pH 4 by addition of concentrated acetic acid and after removal of precipitated material and cell debris by centrifugation or filtration. In a further preferred embodiment, the resin Fractogel EMD SE Hicap is loaded with the fluid comprising the Fc-containing protein adjusted to a pH at about pH 4 and a conductivity of about 15 mS/cm at a dynamic capacity of 40 to 47 g of Fc-containing protein per liter of packed cation exchange resin. The conductivity of the fluid at about 15 mS/cm can be e.g. 15.9, 15.8, 15.7, 15.6, 15.5, 15.5, 15.4, 15.3, 15.2, 15.1, 15, 14.9, 14.8, 14.7, 14.6, 14.5, 14.6, 14.7, 14.6 or 14.5 mS/cm.

In a preferred embodiment of the invention, the Fc-containing fluid loaded on the cation exchange resin in step (a) may be clarified harvest (i.e. clarified cell culture supernatant).

The cation-exchange chromatography is preferably used as a capture step, and thus serves for purification of the Fc-containing protein, in particular to the reduction, decrease or elimination, of host cell proteins, Fc-containing protein aggregates and incomplete fragments of the Fc-containing protein, and for concentration of the Fc-containing protein preparation.

The term "incomplete Fc-containing protein" or "incomplete Fc-containing protein fragments", as used herein, is meant to encompass any part of the Fc-containing protein to be purified in accordance with the present invention, which is derived from the immunoglobulin constant domain or domains without comprising complete further domains. Thus, if the Fc-containing protein comprises immunoglobulin variable domains, incomplete Fc-containing protein fragment does not contain significant portions of the variable domains. If the Fc-containing protein is an Fc-fusion protein, incomplete Fc-containing protein does not contain significant portions of the therapeutic moiety of the Fc-fusion protein. If the Fc-containing protein is an antibody, incomplete Fc-containing fragments are polypeptides comprising only part of the target antibody amino acid sequence. These fragments may arise from the incomplete synthesis of the target antibody, from the cleavage of one or more internal peptide bonds or from the absence of disulphide bridges between independent subunits resulting in, for example, free heavy chain or free light chain for antibodies.

In accordance with the present invention, cation exchange chromatography can preferably be used for elimination or reduction of HCPs in the range of 20 to 350 fold i.e. 20, 40, 60, 80, 100, 120, 140, 160, 180, 200, 220, 240, 260, 280, 300, 320, 340 fold. Thus, the eluate of the cation exchange resin resulting from step (c) has an HCP level of less than 10,000 ppm or less than 9,500 ppm or less than 9,000 ppm or less than 8,500 ppm or 8,000 ppm or less than 7,500 ppm or less than 7,000 ppm or less than 6,500 ppm or less than 6,000 ppm or less than 5,500 or less than 5,000 ppm or less than 4,500 ppm or less than 4,000 ppm.

The cation-exchange chromatography of the invention has the further advantage of reducing aggregate levels by about up to 10 fold. Therefore in a preferred embodiment, the eluate of the cation exchange column has an aggregate level of less than 1% or less than 0.9% or 0.8% or less than 0.7% or less than 0.6% or less than 0.5% or less than 0.5% or less than 0.4% or less than 0.3% or less than 0.2% or less than 0.1%.

In addition, the cation exchange chromatography of the invention reduces the levels of incomplete Fc-containing proteins b below detection levels as determined by SDS-PAGE. Therefore, in a preferred embodiment of the invention, the eluate of the cation exchange chromatography has levels of incomplete Fc-containing protein, that are undetectable by SDS-PAGE under non-reducing conditions and silver staining when loading 1 mcg of Fc-containing protein. The incomplete Fc-containing protein preferably comprises free antibody heavy and/or light chains.

The term "aggregates", as used herein, is meant to refer to protein aggregates, and encompasses multimers of the Fc-containing protein to be purified, e.g. resulting in high molecular weight aggregates.

In a highly preferred embodiment, the method of the invention is used as a first step of a purification scheme of an Fc-containing protein comprising the following steps:

i. Subjecting a fluid comprising said Fc-containing protein and adjusted to a pH of less than 5 or diluted with water until the conductivity is less than 4 mS/cm to cation-exchange chromatography according to the method of the invention;

ii. Subjecting the eluate of step (i) to Anion exchange chromatography or hydrophobic interaction chromatography;

iii. Subjecting the eluate or flow-through of step (ii) to Hydrophobic interaction or Anion exchange chromatography.

In accordance with the present invention, the eluate from the cation exchange chromatography step or from the hydrophobic interaction chromatography step can be subjected further to an anion exchange chromatography. The anion exchange chromatography may be carried out on any suitable anion exchange resin, such as e.g. weak or strong anion exchangers as explained above in the Background of the Invention. Preferably, the anion exchange chromatography is carried out on a strong anion exchange resin. A resin commercially available under the name Poros 50 HQ (from *Applied Biosystems*) is an example of an anion exchange resin that is particularly suitable for the anion exchange chromatography according to the present method.

The anion exchange column is also preferably equilibrated with an appropriate buffer.

Preferably, the eluate from a preceding step is diluted or dialysed into an appropriate loading buffer before loading it on the anion exchange column. The anion exchange column is also preferably equilibrated with the loading buffer. An appropriate equilibration/loading/washing buffer is e.g. sodium phosphate ranging from about 5 to about 25 mM.

From about 5 to 25 mM, the buffer concentration may e.g. be at about 5, 10, 15, 20, 25 mM. A preferred conductivity for the loading buffer is in the range of about 1.0 to about 4.5 mS/cm e.g. 2, 2.5, 3, 3.5, 4 or 4.5 mS/cm.

A suitable pH for the loading buffer range is about 0.5 to 1 unit below the pI. Suitable pH values range from 7.0 to 9.0, preferably from about 7.5 to about 9.0, e.g. about 7.5, 7.55, 7.6, 7.65, 7.7, 7.75, 7.8, 7.85, 7.9, 7.95, 8.0, 8.05, 8.1, 8.15, 8.2, 8.25, 8.3, 8.35, 8.4, 8.45, 8.5, 8.55, 8.6, 8.65, 8.7, 8.75, 8.8, 8.85, 8.9 or 8.95.

An appropriate equilibration/loading/washing buffer may e.g. be sodium phosphate at a concentration of about 5 mM and a pH at about 8.5. The load material is dialysed or diafiltered against such buffer or as an alternative it is diluted with water to a conductivity of about 1. mS/cm. In the frame of the present invention, the flow-through (also called breakthrough) of the anion exchange chromatography, comprising the Fc-containing protein of interest, is collected.

In accordance with the present invention, the eluate from the cation exchange chromatography step or the flow through from the anion exchange chromatography step is then subjected to hydrophobic interaction chromatography. The hydrophobic interaction chromatography may be carried out on any suitable hydrophobic interaction chromatography resin. Two resins commercially available under the name Phenyl Sepharose 6 Fast Flow High sub and Phenyl Sepharose HP (from GE Healthcare) are examples of HIC resins that are particularly suitable for the hydrophobic interaction chromatography step according to the present method.

The hydrophobic interaction chromatography column is preferably equilibrated with an appropriate equilibration buffer.

Preferably, the eluate from a preceding step is diluted, dialysed or diafiltered into an appropriate loading buffer before loading it on the hydrophobic interaction chromatography column e.g. the flow through form the anion exchange chromatography can preferably be diluted into a loading buffer. Prior to its dilution into a loading buffer, the eluate from the cation exchange chromatography bstep is preferably first diafiltered into about 100 mM sodium phosphate at about pH 7.0 and concentrated at about 2 to 4 fold.

An appropriate loading buffer is e.g. a buffer consisting of sodium phosphate at 100 mM and sodium sulfate ($Na_2SO_4$) at 0.5 to 0.6M. Suitable pH values for the equilibration/washing/loading buffer range from about 5.0 to about 8.0, preferably from about 6.5 to about 7.5, e.g. at about 6.5, 6.55, 6.6, 6.65, 6.7, 6.75, 6.8, 6.85, 6.9, 6.95, 7.0, 7.05, 7.1, 7.15, 7.2, 7.25, 7.3, 7.35, 7.4, 7.45 or 7.5. Other anti-chaotropic salts than sodium sulphate may be used such as for example ammonium sulphate (($NH_4)_2SO_4$) at about 1.0 to 1.2M. Alternatively, sodium chloride (NaCl) can also be used at a concentration of about 3.5 to 4M.

After loading, the column is washed with an appropriate wash buffer, and the Fc-containing protein is then eluted from the HIC resin with an appropriate elution buffer. The elution from the HIC column can be isocratic or gradient elution.

An appropriate equilibration/wash buffer can e.g. be 100 mM sodium phosphate at pH 7 containing 0.5 to 0.6M $Na_2SO_4$ or 1.0 to 1.2M $(NH_4)_2SO_4$ or 3.5 to 4.0M NaCl.

The elution from the HIC column can be isocratic or gradient elution. An appropriate elution buffer for the isocratic elution comprises about 5 to about 25, preferably 10, 15 or 20 mM sodium phosphate. When gradient elution is performed, the Fc-containing protein is eluted from the HIC resin with a decreasing salt gradient buffer consisting of about 0.5M to 0M $Na_2SO_4$ or about 1.0 to 0M $(NHK)_2SO_4$ or about 4 to 0M NaCl in about 100 mM to about 10 mM sodium phosphate.

In the frame of the present invention, the eluate of the HIC, comprising the Fc-containing protein of interest, is being collected.

In a preferred embodiment of the invention, the Fc-containing protein has an isoelectric point (pI) between about 7.5 and about 9.5. The pI can be e.g. about 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4 or about 9.5.

The volume of the resin, the length and diameter of the column to be used, as well as the dynamic capacity and flow-rate to be used in the various purification steps of the invention depend on several parameters such as the volume of fluid to be treated, concentration of protein in the fluid to be subjected to the process of the invention, etc. Determination of these parameters for each step is well within the average skills of the person skilled in the art.

In a preferred embodiment of the present purification process, one or more ultrafiltration steps are performed. Ultrafiltration is useful for removal of small organic molecules and salts in the eluates resulting from previous chromatographic steps, to equilibrate the Fc-containing protein in a suitable buffer, or to concentrate the Fc-containing protein to the desired concentration. Such ultrafiltration may e.g. be performed by the technique known as tangential flow filtration (TFF) on membranes, with pore sizes allowing the removal of components having molecular weights below 5, 10, 15, 20, 25, 30 or more kDa.

In a further preferred embodiment, the Fc-containing protein purified according to the method of the invention comprises an Immunoglobulin (Ig) constant region, most preferably human constant region.

The term "Fc-containing protein", as used herein, also refers to any protein having at least one immunoglobulin constant domain selected from the $CH_1$, hinge, $CH_2$, $CH_3$, CH4 domain, or any combination thereof, and preferably a hinge, $CH_2$ and CH3 domain. The immunoglobulin constant domain may be derived from any of IgG, IgA, IgE, IgM, or combination or isotype thereof. Preferably, it is IgG, such as e.g. $IgG_1$, $IgG_2$, $IgG_3$ or IgG. More preferably, it is $IgG_1$.

In a preferred embodiment, the Fc-containing protein comprises an immunoglobulin variable region, e.g. one or more heavy chain variable domains and/or one or more light chain variable domains. Preferably, the Fc-containing protein contains one or two heavy chain variable domains. More preferably, the Fc-containing protein additionally contains one or two light chain constant and/or variable domains.

The term "Fc-containing protein", as used herein, is meant to encompass proteins, in particular therapeutic proteins, comprising an immunoglobulin-derived moiety, which will be called herein the "Fc-moiety", and a moiety derived from a second, non-immunoglobulin protein, which will be called herein the "therapeutic moiety", irrespective of whether or not treatment of disease is intended. The recombinant polypeptide fused to the Fc-moiety may correspond to any polypeptide of interest, in particular for polypeptides for which cellular secretion and/or production in a cell is desired.

Fc-fusion proteins are also Fc-containing proteins that are preferably subjected to the method of the invention.

The Fc-moiety may be derived from a human or animal immunoglobulin (Ig) that is preferably an IgG. The IgG may be an $IgG_1$, $IgG_2$, $IgG_3$ or IgG. The Fc-moiety may comprise all or a part of the constant region domains of an immunoglobulin. It is preferred that the Fc-moiety comprises at least a $CH_2$ and $CH_3$ domain. It is further preferred that the Fc-moiety comprises the Ig hinge region, the $CH_2$ and the $CH_3$ domain. Particularly It is preferred that the Fc-moiety comprises the IgG $CH_2$ and the $CH_3$ domain, with or without the hinge region.

The Fc-containing protein of the invention may be a monomer or dimer. The Fc-containing protein may also be a "pseudo-dimer", containing a dimeric Fc-moiety (e.g. a dimer of two disulfide-bridged hinge-$CH_2$-$CH_3$ constructs), of which only one is fused to a therapeutic moiety. The Fc-containing protein may be a heterodimer, containing two different therapeutic moieties, or a homodimer, containing two copies of a single therapeutic moiety. Preferably, the Fc-fusion protein is a dimer. It is also preferred that the Fc-containing protein of the invention is a homodimer.

In accordance with the present invention, the Fc-moiety may also be modified in order to modulate effector functions. For instance, the following Fc mutations, according b EU index positions (Kabat et al., 1991), can be introduced if the Fc-moiety is derived from $IgG_1$:

T250Q/M428L
M252Y/S254T/T256E+H433K/N434F
E233P/L234WL235A/?G236+A327G/A330S/P331S
E333A; K322A.

Further Fc mutations may e.g. be the substitutions a EU index positions selected from 330, 331 234, or 235, or combinations thereof. An amino acid substitution at EU index position 297 located in the $CH_2$ domain may also be introduced into the Fc-moiety in the context of the present invention, eliminating a potential site of N-linked carbohydrate attachment. The cysteine residue at EU index position 220 may also be replaced with a serine residue, eliminating the cysteine residue that normally forms disulfide bonds with the immunoglobulin light chain constant region.

The therapeutic moiety of the Fc-containing protein may e.g. be or be derived from EPO, TPO, Growth Hormone, Interferon-alpha, Interferon-beta, Interferon-gamma, PDGF-beta, VEGF, IL-1alpha, IL-1beta, IL-2, IL-4, IL-5, IL-8, IL-10, IL-12, IL-18, L-18 binding protein, TGF-beta, TNF-alpha, or TNF-beta.

The therapeutic moiety the Fc-containing protein may also be derived from a receptor, e.g. a transmembrane receptor, preferably be or be derived from the extracellular domain of a receptor, and in particular a ligand binding fragment of the extracellular part or domain of a given receptor. Examples for therapeutically interesting receptors are CD2, CD3, CD4, CD8, CD11a, CD14, CD18, CD20, CD22, CD23, CD25, CD33, CD40, CD44, CD52, CD74, CD80, CD86, CD147, CD164, IL-2 receptor, IL-4 receptor, IL-6 receptor, IL-12 receptor, IL-18 receptor subunits (IL-18R-alpha, IL-18R-beta), EGF receptor, MIF receptor, VEGF receptor, integrin alpha 410 beta 7, the integrin VLA4, B2 integrins, TRAIL receptors 1, 2, 3, and 4, RANK, RANK ligand, epithelial cell adhesion molecule (EpCAM), intercellular adhesion molecule-3 (ICAM-3), CTLA4 (which is a cytotoxic T lymphocyte-associated antigen), Fc-gamma-1 receptor, HLA-DR 10 beta, HLA-DR antigen, L-selectin, a fragment of a receptor belonging to the TNFR superfamily such as, e.g., a fragment derived from the extracellular domain of TNFR1 (p55), TNFR2 (p75), OX40, Osteoprotegerin, CD27, CD30, CD40, RANK, DR3, Fas ligand, TRAIL-R1, TRAIL-R2, TRAIL-R3, TAIL-R4, NGFR, AITR, BAFFR, BCMA or TACI.

Therapeutic Fc-fusion proteins, i.e. Fc-fusion proteins intended for treatment or prevention of disease of an animal or preferably for human treatment or administration, are especially suitable for use in the frame of the invention, to be purified in accordance with the invention.

Most preferably, said Fc-fusion protein comprises either a fragment of the TACI receptor (see e.g. WO 02/094852) or a fragment of IFNbeta (see e.g. WO 2005/001025).

In a preferred embodiment of the invention, the Fc-containing protein that can be purified according to the invention is an antibody. Preferably, said antibody is a monoclonal antibody. The antibody may be a chimeric antibody, a humanized antibody or a human antibody. The antibody may either be produced in a host cell transfected with one, two or more polynucleotides coding for the antibody or produced from a hybridoma.

As used herein, the term "antibody" refers to a Fc-containing protein wherein the therapeutic moiety comprises at least one variable domain of an immunoglobulin (Ig). Preferred immunoglobulins are mammalian immunoglobulins. More preferred immunoglobulins are camelid immunoglobulins. Even more preferred immunoglobulins are rodent immunoglobulins, in particular from rat or mouse. Most preferred immunoglobulins are primate immunoglobulins, in particular human immunoglobulins.

The term "antibody" refers to an immunoglobulin or fragment thereof, and encompasses any polypeptide comprising an antigen-binding site. The term includes, but is not limited to, polyclonal, monoclonal, monospecific, polyspecific, non-specific, humanized, human, chimeric, single-chain, synthetic, recombinant, hybrid, mutated, grafted, or in vitro generated antibodies. The antibody may be selected from any of the known antibody classes, for example, IgA, IgG, IgD, IgE, IgM. The antibody may be a monomer, dimer, or multimer such as a trimer, or pentamer.

An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions retain the binding specificity to the antigen and can be further subdivided into regions of hypervariability, termed complementarity determining regions (CDR) The CDRs are interspersed with regions that are more conserved, termed framework regions (FR). Each VH and VL is composed of three CDRs and four framework regions, arranged from amino-terminus to carboxy-terminus in the following order: FR1, CDR1, FR2, CDR2, FR3, CDR3, FR4. The variable regions of the heavy and light chains contain a binding domain that interacts with an antigen.

Examples of antibodies that can be purified in accordance with the present invention are antibodies directed against a protein selected from the group consisting of CD3 (e.g. OKT3, NI-0401), CD11a (e.g. efalizumab), CD4 (e.g. zanolimumab, TNX-355), CD20 (e.g. ibritumomab tiuxetan, rituximab, tositumomab, ocrelizumab, ofatumumab, IMMU-106, TRU-015, AME-133, GA-101), CD23 (e.g. lumiliximab), CD22 (e.g. epratuzumab), CD25 (e.g. basiliximab, daclizumab), the epidermal growth factor receptor (EGFR) (e.g. panitumumab, cetuximab, zalutumumab, MDX-214), CD30 (e.g MDX-060), the cell surface glycoprotein CD52 (e.g. alemtuzumab), CD80 (e.g. galiximab), the platelet GPIIb/IIIa receptor (e.g. abciximab), TNF alpha (e.g. infliximab, adalimumab, golimumab), the interleukin-6 receptor (e.g. tocilizumab), carcinoembryonic antigen (CEA) (e.g. 99 mTc-besilesomab), alpha-4/beta-1 integrin (VLA4) (e.g. natalizumab), alpha-5/beta-1 integrin (VLA5) (e.g. volociximab), VEGF (e.g. bevacizumab, ranibizumab), immunoglobulin E (IgE) (e.g. omalizumab), HER-2/neu (e.g. trastuzumab), the prostate specific membrane antigen (PSMA) (e.g. 111In-capromab pendetide, MDX-070), CD33 (e.g. gemtuzumab ozogamicin), GM-CSF (e.g. KB002, MT203), GM-CSF receptor (e.g. CAM-3001), EpCAM (e.g. adecatumumab), IFN-gamma (e.g. NI-0501), IFN-alpha (e.g. MEDI-545/MDX-1103), RANKL (e.g. denosumab), hepatocyte growth factor (e.g. AMG 102), IL-15 (e.g. AMG 714), TRAIL (e.g. AMG 655), insulin-like growth factor receptor (e.g. AMG 479, R1507), IL-4 and IL13 (e.g. AMG 317), BAFF/BLyS receptor 3 (BR3) (e.g. CB1), CTLA-4 (e.g. ipilimumab).

Preferably, the antibodies that can be purified in accordance with the present invention are antibodies directed against a protein selected from the group consisting of CD3, CD4, CD11a, CD25, IFN-gamma, EpCAM, TACI.

Most preferably, said antibody is selected from the group consisting of an anti-CD4 antibody (see e.g. WO 97/13852), an anti-CD11a antibody (see e.g. WO 98/23761) and an anti-CD25 antibody (see e.g. WO 2004/045512).

In a preferred embodiment, the antibody to be purified is anti-CD25 rhAb of the IgG1 subclass having a human heavy chain variable region comprising the amino acid sequence as set forth in SEQ ID NO: 1 and human kappa light chain variable region comprising the amino acid sequence as set forth in SEQ ID NO: 2, or conservative sequence modifications thereof.

In yet a further preferred embodiment, the antibody is anti CD-25 antibody comprising (i) VH CDR1 of SEQ ID NO: 3, the VH CDR2 of SEQ ID NO: 4 and the VH CDR3 of SEQ ID NO: 5 and VL CDR1 of SEQ ID NO: 6, the VL CDR2 of SEQ ID NO: 7 and the VL CDR3 of SEQ ID NOS: 8; or (ii) conservative sequence modifications of any one of the sequences defined in (i).

Antibodies directed against TNF, Blys, or Interferon-γ are further examples of therapeutically interesting antibodies.

If the protein purified according to the process of the invention is intended for administration to humans, it is advantageous to include one or more steps of virus removal in the process.

In order to facilitate storage or transport, for instance, the material may be frozen and thawed before and/or after any purification step of the invention.

In accordance with the present invention, the recombinant Fc-containing protein may be produced in eukaryotic expression systems, such as yeast, insect, or mammalian cells, resulting in glycosylated Fc-containing proteins.

In accordance with the present invention, it is most preferred to express the Fc-containing protein in mammalian cells such as animal cell lines, or in human cell lines. Chinese hamster ovary cells (CHO) or the murine myeloma cell line NS0 are examples of cell lines that are particularly suitable for expression of the Fc-containing protein to be purified. The Fc-containing protein can also preferably be produced in human cell lines, such as e.g. the human fibrosarcoma HT1080 cell line, the human retinoblastoma cell line PERC6, or the human embryonic kidney cell line 293, or a permanent aminocyte cell line as described e.g. in EP 1 230 354.

If the Fc-containing protein to be purified is expressed by mammalian cells secreting it, the starting material of the purification process of the invention is cell culture supernatant, also called harvest or crude harvest. If the cells are cultured in a medium containing animal serum, the cell culture supernatant also contains serum proteins as impurities.

Preferably, the Fc-containing protein expressing and secreting cells are cultured under serum-free conditions. The Fc-containing protein may also be produced in a chemically defined medium. In this case, the starting material of the purification process of the invention is serum-free cell culture supernatant that mainly contains host cell proteins as impurities. If growth factors are added to the cell culture medium, such as insulin, for example, these proteins will be eliminated during the purification process as well.

In order to create soluble, secreted Fc-containing protein, that are released into the cell culture supernatant, either the natural signal peptide of the therapeutic moiety of the Fc-containing protein is used, or preferably a heterologous signal peptide, i.e. a signal peptide derived from another secreted protein being efficient in the particular expression system used, such as e.g. the bovine or human Growth Hormone signal peptide, or the immunoglobulin signal peptide.

Conservative sequence modifications of any or conservative amino acid substitutions may include synonymous amino acids within a group which have sufficiently similar physicochemical properties that substitution between members of the group will preserve the biological function of the molecule (Grantham, 1974).

The Fc-containing protein to be purified in accordance with the present invention, may also be modified at functional groups which occur as side chains on the residues or the N or C-terminal groups, by means known in the art. Such modified Fc-containing proteins and are included in the invention as long as they do not destroy the activity of the protein which is substantially similar to the activity of the unmodified Fc-containing protein as defined above, and do not confer toxic properties on compositions containing it.

For example, Fc-containing protein can e.g. be conjugated to polymers in order to improve the properties of the protein, such as the stability, half-life, bioavailability, tolerance by the human body, or immunogenicity. To achieve this goal, the Fc-containing protein may be linked e.g. to polyethylene glycol (PEG). PEGylation may be carried out by known methods, described in WO 92/13095, for example.

In a second aspect, the invention relates to the use of a cation exchange chromatography for capturing an Fc-containing protein from a fluid wherein, following binding of the Fc-containing protein to the cation exchange resin, the resin is washed with a buffer at a pH of about 1 unit below the isoelectric point of the Fc-containing protein. The Fc-containing protein is preferably eluted from the resin in a salt gradient. In addition, cutting out the tail of the elution peak can be performed.

The invention further relates to a protein purified by the purification method according to the invention. In the following, such protein is also called "purified Fc-containing protein".

Such purified Fc-containing protein is preferably highly purified Fc-containing protein. Highly purified Fc-containing protein is determined e.g. by the presence of a single band in a silver-stained, non-reduced SDS-PAGE-gel after loading of protein in the amount of 2 mcg per lane. Purified Fc-containing protein may also be defined as eluting as a single peak in HPLC.

The Fc-containing protein preparation obtained from the purification process of the invention may contain less than 20% of impurities, preferably less than 10%, 5%, 3%, 2% or 1% of impurities, or it may be purified to homogeneity, i.e. being free from any detectable proteinaceous contaminants.

Purified Fc-containing protein may be intended for therapeutic use, in particular for administration to human patients. If purified Fc-containing protein is administered to patients, it is preferably administered systemically, and preferably subcutaneously or intramuscularly, or topically, i.e. locally. Rectal or intrathecal administration may also be suitable, depending on the specific medical use of purified Fc-containing protein.

For this purpose, in a preferred embodiment of the present invention, the purified Fc-containing protein may be formulated into pharmaceutical composition, i.e. together with a pharmaceutically acceptable carrier, excipients or the like.

The definition of "pharmaceutically acceptable" is meant to encompass any carrier, which does not interfere with effectiveness of the biological activity of the active ingredient and that is not toxic to the host to which it is administered. For example, for parenteral administration, the active protein(s) may be formulated in a unit dosage form for injection in vehicles such as saline, dextrose solution, serum albumin and Ringer's solution.

The active ingredients of the pharmaceutical composition according to the invention can be administered to an individual in a variety of ways. The routes of administration include intradermal, transdermal (e.g. in slow release formulations), intramuscular, intraperitoneal, intravenous, subcutaneous, oral, intracranial, epidural, topical, rectal, and intranasal routes. Any other therapeutically efficacious route of administration can be used, for example absorption through epithelial or endothelial tissues or by gene therapy wherein a DNA molecule encoding the active agent is administered to the patient (e.g. via a vector), which causes the active agent to be expressed and secreted in vivo. In addition, the protein(s) according to the invention can be administered together with other components of biologically active agents such as pharmaceutically acceptable surfactants, excipients, carriers, diluents and vehicles.

For parenteral (e.g. intravenous, subcutaneous, intramuscular) administration, the active protein(s) can be formulated as a solution, suspension, emulsion or lyophilized powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

The therapeutically effective amounts of the active protein(s) will be a function of many variables, including the type of Fc-containing protein, the affinity of the Fc-containing protein for its ligand, the route of administration, the clinical condition of the patient.

A "therapeutically effective amount" is such that when administered, the Fc-containing protein results in inhibition of its ligand of the therapeutic moiety of the Fc-fusion protein, as explained above.

The dosage administered, as single or multiple doses, to an individual will vary depending upon a variety of factors, including pharmacokinetic properties of the Fc-containing protein, the route of administration, patient conditions and characteristics (sex, age, body weight, health, size), extent of symptoms, concurrent treatments, frequency of treatment and the effect desired. Adjustment and manipulation of established dosage ranges are well within the ability of those skilled in the art, as well as in vitro and in vivo methods of determining the inhibition of the natural ligand of the therapeutic moiety in an individual.

Purified Fc-containing protein may be used in an amount of about 0.001 to 100 mg/kg or about 0.01 to 10 mg/kg or body weight, or about 0.1 to 5 mg/kg of body weight or about 1 to 3 mg/kg of body weight or about 2 mg/kg of body weight.

In further preferred embodiments, the purified Fc-containing protein maybe administered daily or every other day or three times per week or once per week.

The daily doses are usually given in divided doses or in sustained release form effective to obtain the desired results. Second or subsequent administrations can be performed at a dosage which is the same, less than or greater than the initial or previous dose administered to the individual. A second or subsequent administration can be administered during or prior to onset of the disease.

The present invention further relates to the use of cation exchange chromatography for the reduction of the concentration of HCPs, aggregates and incomplete Fc-containing protein fragments in a composition comprising an Fc-containing protein.

In a preferred embodiment, the HCP levels are reduced to less than 10,000 ppm or less than 9,500 ppm or less than 9,000 ppm or less than 8,500 ppm or 8,000 ppm or less than 7,500 ppm or less than 7,000 ppm or less than 6,500 ppm or less than 6,000 ppm or less than 5,500 or less than 5,000 ppm or less than 4,500 ppm or less than 4,000 ppm. Aggregate level are reduced to less than 1% or less than 0.9% or 0.8% or less than 0.7% or less than 0.6% or less than 0.5% or less than 0.5% or less than 0.4% or less than 0.3% or less than 0.2% or less than 0.1%. Levels of incomplete Fc-containing proteins such as free heavy and/or free light chains are reduced to below detection levels as determined by SDS-PAGE under non-reducing conditions and silver staining with a load of 1 mcg Fc-containing protein.

Having now fully described this invention, it will be appreciated by those skilled in the art that the same can be performed within a wide range of equivalent parameters, concentrations and conditions without departing from the spirit and scope of the invention and without undue experimentation.

While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning a range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

EXAMPLES

Purification of Recombinant Antibodies from Serum-Free CHO Cell Supernatant

| List of abbreviations frequently used throughout the examples | |
|---|---|
| Ab: | Antibody |
| AEX: | anion-exchange chromatography |
| BV: | bed volume |
| CEX: | cation-exchange chromatography |
| CHO: | Chinese Hamster Ovary |
| Cond.: | Conductivity |
| ELISA: | Enzyme-Linked ImmunoSorbent Assay |
| HCP: | Host Cell Protein |
| HIC: | hydrophobic interaction chromatography. |
| K: | potassium |
| kD: | kilo Dalton |
| Na: | sodium |
| NaAc: | Sodium Acetate |
| NaCl: | Sodium chloride |
| SE-HPLC: | Size-Exclusion High Performance Liquid Chromatography (Ab Aggregates quantification) |
| ppm: | parts per million |
| rh: | Recombinant human |
| RT: | Room Temperature |

-continued

| List of abbreviations frequently used throughout the examples | |
|---|---|
| SDS-PAGE: | Sodium Dodecyl Sulphate Polyacrylamide Gel Electrophoresis |
| SE-HPLC: | Size-Exclusion High Performance Liquid Chromatography |
| UV: | Ultra-Violet |

Equipment

Äkta explorer 100 (GE Healthcare)

Fraction Collector Frac-950 (GE Healthcare)

XK16 chromatography column, 1.6 cm diameter (GE Healthcare)

0.66 cm chromatography column (Omnifit)

Digital Balance PM6100 (Mettler)

712 Conductometer (Metrohm)

713 pH meter (Metrohm)

Example 1

Capture Step—Cation-Exchange Chromatography—Elution Conditions

Cation exchange chromatography was used for the capture of an anti-CD25 recombinant human monoclonal antibody (anti-CD25 rhAb) produced in CHO cells. The objective of this experiment was to evaluate the effect of the pH of the elution buffer on the yield and the purity (i.e. content of HCPs) of the capture step. Five different elution conditions were tested according to the following protocol:

Starting material was clarified harvest of Anti-CD25 rhAb having human γ1 heavy chain variable region comprising the amino acid sequence as set forth in SEQ ID NO: 1 and human kappa light chain variable regions comprising the amino acid sequence as set forth in SEQ ID NO: 2. The molecular weight of the human monoclonal antibody expressed in CHO cells under serum-free conditions was of about 150 kilodalton (kDa) and an isoelectric point (pI) of approximately 9. All the operations were performed at room temperature and the flow rate was kept constant at 100 cm/h. The UV signal at 280 nm was recorded at all time.

Column

Fractogel EMD SE Hicap (M) resin (Merck) was packed into a 1.4 ml volume column of 0.66 cm diameter having a bed height of 4 cm.

Buffers

A1=20 mM citrate/phosphate at pH 5.0, pH 6.0, pH 7.0, or pH 8.0

A2=0.5 M NaOH

B1=20 mM citrate/phosphate+1 M NaCl, pH 5.0, 6.0, 7.0 or 8.0

Equilibration

The column was equilibrated with at least 10 BV of the adequate Buffer A1.

Loading 70 ml of anti-CD25 rhAb harvest at a titer of about 1 g/L, first adjusted to pH 4.5 by the addition of concentrated acetic acid and 0.22 μm filtered (cond. 15.0 mS/cm). The load capacity was 47 mg of anti-CD25 rhAb as determined by Biacore assay per ml of packed resin.

Wash Step

The column was washed with at least 10 BV of the adequate Buffer A1.

Elution

The column was eluted in a linear NaCl gradient (see table 1, column 1) with 25 BV of buffer A1 to buffer B1 at pH 5.0, 6.0, 7.0 or 8.0 followed by 5 BV of buffer B1. 1.4 ml fractions were collected.

Regeneration & Sanitisation

The column was regenerated with 5 BV of Buffer A2.

Re-Equilibration

The column was re-equilibrated with at least 5 BV of the adequate Buffer A1.

Results

The elution of the anti-CD25 rhAb from the capture column was realized by an increasing NaCl gradient in the conditions set forth below. An isocratic elution (pH and salt concentration constant) was also tested.

TABLE 1

Elution results from the capture step using different elution conditions

| Elution Buffer (B1) | Sample type | Anti-CD25 rhAb concentration (mg/L) | Anti-CD25 rhAb Yield (%) | HCP (ppm) | % HCPs in the fraction collected |
|---|---|---|---|---|---|
|  | Starting Material | 951 |  | 261705 |  |
| Salt Gradient | Elution Peak Shoulder | 846 | 4 | 176067 | 2.4 |
| 0 to 1 M NaCl | Elution Peak | 12600 | 79 | 97584 | 29.6 |
| pH 5.0 | Peak Tail | 865 | 13 | 665618 | 32.4 |
| Salt Gradient | Wash shoulder | <0.5 | 0 | <861600 | 0.0 |
| 0 to 0.8 M NaCl | Wash Peak | <0.5 | 0 | <120448000 | 1.5 |
| pH 6.0 | Start Elution Peak | 169 | 1 | 722062 | 2.0 |
|  | Elution Peak | 10600 | 111 | 44464 | 18.9 |
|  | Elution Peak tail | 195 | 2 | 3381101 | 31.8 |
| Salt Gradient | Wash Peak | 3.8 | 0 | 76642447 | 7.0 |
| 0 to 0.6 M NaCl | Start Elution Peak | 76.8 | 0 | 517266 | 0.6 |
| pH 7.0 | Elution Peak | 6410 | 94 | 46859 | 16.9 |
|  | Elution Peak tail | 288 | 3 | 1700708 | 19.7 |
| Salt Gradient | Wash Peak | 14.9 | 0 | 13281208 | 6.4 |
| 0 to 0.45 M | Start Elution Peak | 467 | 2 | 71422 | 0.5 |
| NaCl | Elution Peak | 5780 | 85 | 20502 | 6.7 |
| pH 8.0 | Elution Peak tail | 276 | 4 | 1428406 | 22.2 |
| Isocratic 0.35 | Wash Peak | 13.5 | 0 | 18414815 | 6.0 |
| M NaCl | Elution Peak | 9160 | 96 | 76591 | 28.2 |
| pH 8.0 | Elution Peak tail | <0.5 | <0.1 | <31008000 | 7.5 |

FIG. 1 shows overlapping chromatograms of the wash and elution step experiments at the conditions shown in Table 1 (except for the isocratic elution).

As shown in Table 1 above, the antibody yield obtained for all elution conditions (salt gradient or isocratic), was greater than 79%. The wash step at pH 8 followed by gradient elution resulted in a purity of 20500 ppm HCPs in the elution peak, a level 4.7 times lower than the one obtained at pH 5 i.e. 97600 ppm. These results correlate with the largest wash peak in FIG. 1 that corresponds to the conditions at pH 8. At the same pH (Table 1), the use of a gradient rather than isocratic elution allowed the elimination of more HCPs. This is because HCPs were removed not only during the wash step (6.4%) but also in the tail of the elution peak (22.2%).

Conclusion

Wash and elution conditions were optimized to maximize the recovery of product while providing significant HCP clearance.

Example 2

Capture Step—Cation-Exchange Chromatography—"Scale-Up"

The optimized elution conditions from example 1 were used to capture Anti-CD25 rhAb using a column scaled-up from 1.4 to 20 ml.

Starting material was clarified harvest of Anti-CD25 rhAb expressed in CHO cells cultured under serum-free conditions. All the operations were performed at room temperature and the flow rate was kept constant at 150 cm/h. The UV signal at 280 nm was recorded at all time.

Column

Fractogel EMD SE Hicap (M) resin (Merck) was packed into a 20 ml volume column of 1.6 cm diameter having a bed height of 10 cm.

Buffers

A1=100 mM NaAc+128 mM NaCl, pH 4.0, Conductivity 14.7 mS/cm

A2=0.5 M NaOH+2 M KCl

A3=20 mM phosphate, pH 8.0

B1=20 mM phosphate+1 M NaCl, pH 8.0

Equilibration

The column was equilibrated with at least 10 BV of Buffer A1 (or until the target conductivity of 14.7 mS/cm and pH 4.0±0.1 are reached).

Loading

Prior to loading, the anti-CD25 rhAb clarified harvest at a titer of 1 g/L was first adjusted to pH 4.0 by the addition of concentrated acetic and 0.22 µm filtered. The column was loaded at 80% of its dynamic capacity i.e. 36.7 mg of anti-CD25 rhAb per ml of packed resin with anti-CD25 rhAb adjusted harvest with a conductivity of 15.0 mS/cm.

Wash Step

The column was washed with 20 BV of Buffer A3.

Elution

The column was eluted in a concentration gradient of Buffer B1 from 0 to 15% over 25 BV (i.e. 0 to 150 mM NaCl in 20 mM phosphate pH8). 15 ml fractions were collected.

Regeneration

The column was regenerated with 5 BV of Buffer B1 at 100% (i.e. 1 M NaCl).

Sanitisation

Then, the column was sanitised with at least 3 BV of Buffer A2 (0.5 M NaOH+2 M KCl) in up-flow mode. After 1 hour of incubation the column was rinsed with 2 BV of Buffer A2.

Re-Equilibration

The column was re-equilibrated with at least 5 V of Buffer A1

Results

The results in terms of antibody yield, HCP and aggregate clearance are shown in Table 2:

TABLE 2

| Sample type | Biacore Ab yield (%) | HCPs (ppm) | HCPs Elimination factor (clearance) | % HCPs | Aggregates (%) |
|---|---|---|---|---|---|
| Harvest | | 724905 | | | |
| Harvest adjusted to pH 4 | 93 | 1122812 | | | |
| Flow-through | 0 | 5947984 | 0.2 | 1.1 | |
| Wash | 3 | 7593091 | 0.1 | 25.3 | 0.0 |
| Elution peak | 89 | 9462 | 118.7 | 0.9 | 0.2 |
| Elution peak tail | 5 | 133265 | 8.4 | 0.7 | 7.6 |

This capture step was optimized by the selection of the Fractogel EMD SE Hicap resin on the basis of its capacity at 5% breakthrough of 47 mg/ml at pH 4.0 (results not shown) and the conditions of wash in 20 mM sodium phosphate pH 8 and elution in a NaCl gradient at pH 8.0 allow a better elimination of HCPs. The adjustment of the pH of clarified harvest to 4.0, necessary to maximize the load capacity, caused the formation of an important precipitate which was removed by filtration on a 0.22 µm filter. However, despite the precipitate, the recovery of anti-CD25 rhAb was 93%.

Figure 2:
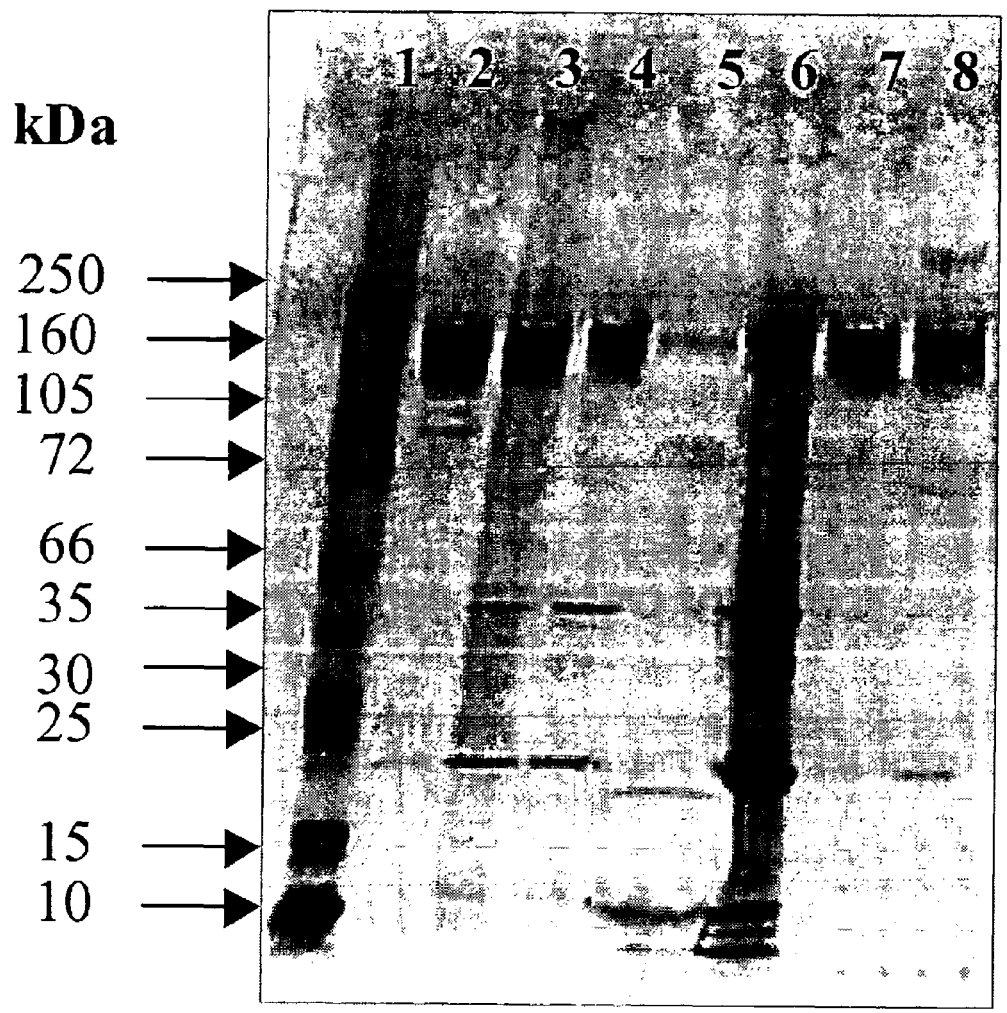
FIG. 2: shows a non-reduced silver stained SDS-PAGE of different fractions produced during the cation exchange chromatography capture step described in Example 2.
  Lane 1: Molecular weight markers
  Lane 2: Standard anti-CD25 rhAb
  Lane 3: Antibody anti-CD25 harvest
  Lane 4: Antibody anti-CD25 harvest adjusted to pH4
  Lane 5: Flow-through
  Lane 6: wash
  Lane 7: Elution peak
  Lane 8: Elution peak tail
Figure 3:
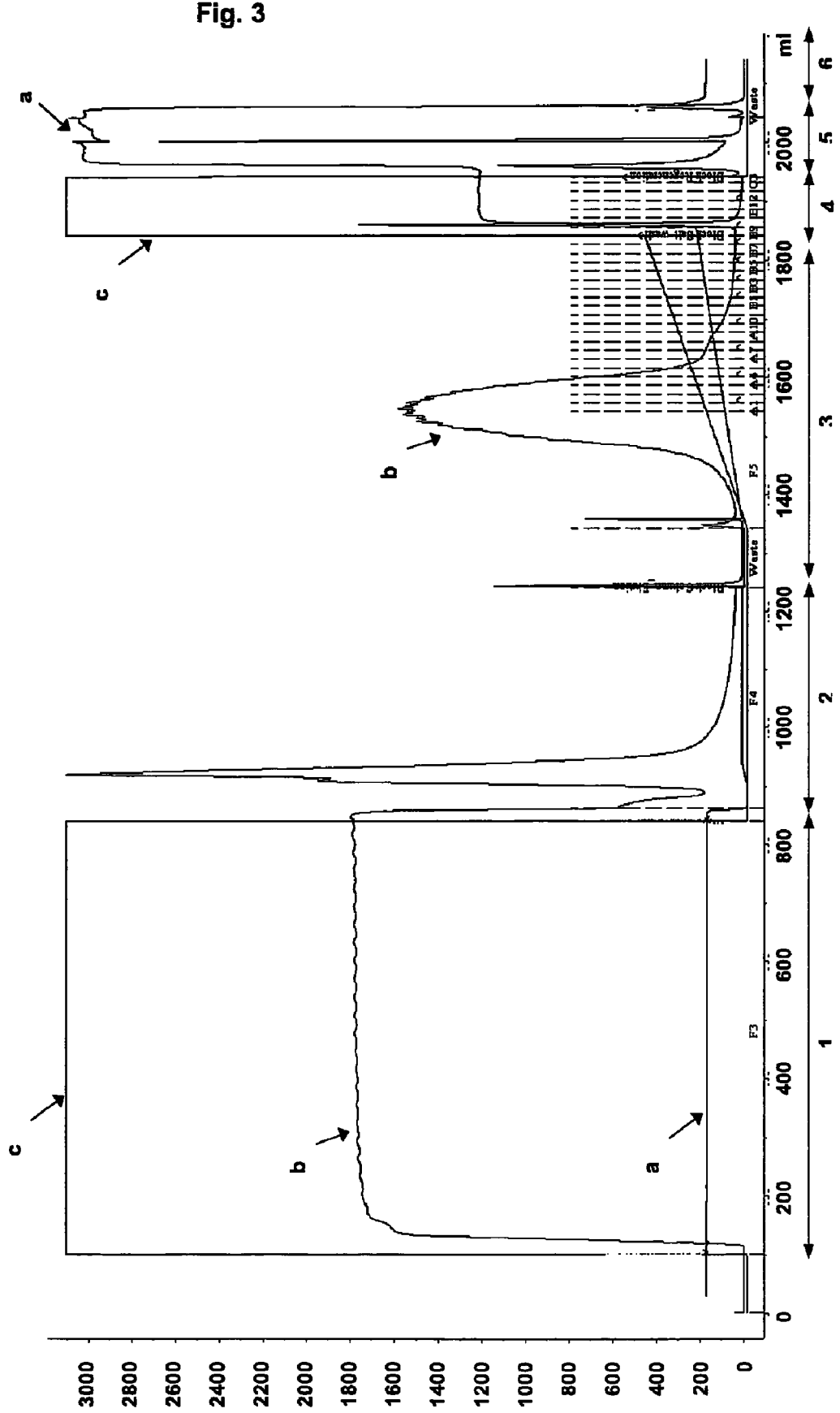
FIG. 3: Shows the chromatographic profile of the cation exchange chromatography described in Example 2. (a) Conductivity (mS/cm), (b) OD at 280 nm, (c) Buffer B1(%). 1—Load, 2—Wash, 3—Elution, 4—Regeneration, 5—Sanitisation, 6—Re-equilibration.

In the chromatogram of the capture step (FIG. 3) a substantial peak of absorbance at 280 nm (i.e. protein) was observed during the wash step. The SDS-PAGE profile of FIG. 2, shows that the wash step resulted in the removal of low molecular-weight proteins including the free heavy chain and the free light chain of the antibody (bands at approximately 50 and 25 kDa respectively) as well as HCPs. These 2 bands are absent in the elution peak (lane 7). The wash step allowed removal of antibody fragments (including free light and free heavy chains) as well as HCPs (see Table 2).

As shown in FIG. 2, lane 7, the product of the elution is relatively pure as there is only one main band at 150 kDa, which corresponds to the anti-CD25 rhAb.

The antibody yield after the capture step was 89% (Table 2). With the wash step and by cutting out the elution peak tail, the HCP levels were reduced by a factor of 119 compared to the clarified harvest adjusted to pH 4.0 to a final level of less than 10,000 ppm. Finally, the level of aggregates in the capture eluate was 0.2%. The tail of the elution peak showed a distinct shoulder (see chromatogram), which contains high levels of aggregates and HCPs and if this fraction is not pooled with the eluate fraction, a product of high purity is obtained.

Conclusion

With the conditions developed for the capture step on CEX, the following impurities have been reduced to very low levels:
HCPs (<10,000 ppm)
aggregates (<1%)
antibody fragments such as heavy chain and light chain (undetected by SDS-PAGE under non-reducing conditions and silver staining).

Example 3

Three Step Purification Process: CEX-AEX-HIC (Process 1)

A three step purification process was developed for the purification of recombinant antibodies. The first step, the capture step on CEX, was followed by an AEX and HIC step in 2 possible orders: CEX-AEX-HIC or CEX-HIC-AEX. In this Example, the CEX capture step was followed by AEX and HIC steps.

3.1 Step 1: Cation Exchange Chromatography

Capture step as described in Example 2.

3.2 Step 2: Anion Exchange Chromatography

Starting Material

The eluate from the capture step on CEX (Example 2), dialysed into a suitable loading buffer (5 mM sodium phosphate pH 8.5), was used as a starting material for the anion exchange chromatography.

Column

Poros 50 HQ resin (Applied Biosystems) was packed to 20 ml volume in a column of 10 cm bed height and 1.6 cm diameter.

All the operations were performed at room temperature and the flow rate was kept constant at 150 cm/h. The UV signal at 280 nm was recorded at all time.

Buffers

A1=5 mM phosphate, pH 8.5, Cond. 1.1 mS/cm
A2=0.5 M NaOH
A3=0.5 M phosphate, pH 8.5

Equilibration

The column was equilibrated with at least 10 BV of Buffer A1 (5 mM phosphate, pH 8.5 or until the target conductivity of 1.1 mS/cm and pH 8.5±0.1 are reached).

Loading, washing and concomitant collection of anti-CD25 rhAb in the flow through The column was loaded with post capture material at a concentration of 1.5 g/L, in 5 mM phosphate buffer, at pH 8.5 (pH at 8.5±0.1, conductivity at 1.1±1 mS/cm). The column was then washed with 10 BV of Buffer A1. The flow-through and wash fractions were collected.

Elution

The column was eluted with 5 BV of buffer A3.

Sanitisation

The column was sanitised with 5 BV of buffer A2.

Pre-equilibration

The column was pre-equilibrated with 5 BV of buffer A3.

Re-Equilibration

The column was re-equilibrated with 5 BV of buffer A1.

3.3 Step 3: Hydrophobic Interaction Chromatography.

Starting Material

The starting material used for this purification step was anion-exchange chromatography flow-through (see Example 3.2).

Column

Phenyl Sepharose 6 Fast Flow High sub resin (GE Healthcare) was packed to 1.4 ml volume in a column of 0.66 cm diameter and a bed height of 4 cm.

All the operations were performed at room temperature and the flow rate was kept constant at 100 cm/h. The UV signal at 280 nm was recorded at all time.
Buffers
A1=100 mM phosphate, pH 7.0
A2=0.5 M NaOH
A3=10 mM phosphate, pH 7.0
B1=100 mM phosphate+1 M $Na_2SO_4$, pH 7.0
Equilibration
The column was equilibrated with 10 BV of a mix between buffer A1 and buffer B1 (50% each).
Loading
The column was loaded with the anion exchange chromatography flow-through of Example 3.2 diluted twice in buffer B1. The column was loaded at 80% capacity (i.e. 16.3 mg of anti-CD25 rhAb per ml of packed resin).
Wash Step
The column was washed with 5 BV of a mix between buffer A1 aid buffer B1 (50% each).
Elution
The column was eluted in a concentration gradient of Buffer B1 from 50 to 0% over 20 BV. 1 BV fractions were collected followed by a wash with 5 BV of buffer A3.
Sanitisation and Regeneration
Sanitisation with 5 BV of buffer A2. After 1 hour of incubation the column was rinsed with 3 BV of water.
Re-Equilibration
The column was re-equilibrated with 5 BV of a mix between buffer A1 and buffer B1 (50% each).

Example 4

Three Step Purification Process: CEX-HIC-AEX
(Process 2)

In this process, the CEX capture step of Example 2 was followed by a HIC and finally by an AEX step. The same protocols as the ones described in Example 3.2 and Example 3.3 were followed with the exception of a few different parameters.

4.1 Step 1: Cation Exchange Chromatography
Capture step as described in Example 2
4.2 Step 2: Hydrophobic Interaction Chromatography (HIC)
The eluate from the capture step on CEX (Example 2) was diafiltered in 100 mM phosphate buffer at pH 7.0 and concentrated (about 4 fold). The steps described in Example 3.3 above were then followed with the following differences: column size, elution (isocratic instead of gradient).

Column
Phenyl Sepharose 6 Fast Flow High sub resin (GE Healthcare) was packed to 20 ml volume in a column of 1.6 cm diameter and a bed height of 10 cm.
Loading
The column was loaded with the eluate from the CEX capture step diafiltered and diluted twice in buffer B1 (100 mM phosphate+1 M $Na_2SO_4$) at pH 7.0. The column was loaded at 80% capacity (i.e. 16.3 mg of anti-CD25 rhAb per ml of packed resin).
Elution
The column was eluted with 15 BV of buffer A3 and 15 ml fractions were collected.
4.2 Step 3: Anion Exchange Chromatography
As the last step of the process, the AEX was realised at a smaller scale and at a lower flow rate (i.e. 100 cm/h). The step of example 3.2 above was followed except for a few differences:
Column
Poros 50 HQ resin (Applied Biosystems) was packed to 1.4 ml volume in a column of 4 cm bed height and 0.66 cm diameter.
Loading
The column was loaded with the eluate from the HIC step (Example 4.2) at a concentration of 2.4 g/L, dialysed into 5 mM phosphate buffer, at pH 8.5 (pH at 8.5±0.1, conductivity at 1.1±1 mS/cm).

Results

Examples 3 and 4

Two processes for the purification of antibodies were tested. In both cases, the capture step on CEX was followed by 2 chromatography steps in one of the following sequences: AEX-HIC (Process 1) or HIC-AEX (Process 2). The results of the processes in terms of antibody yield, HCPs and aggregates are shown in Table 3 below:

TABLE 3

| | Sample type | Ab yield by OD280 nm (%) | Ab yield by Biacore (%) | HCPs (ppm) | HCPs clearance factor (x) | Aggregates (%) |
| --- | --- | --- | --- | --- | --- | --- |
| Process 1 | Harvest | | | 72905 | | |
| CEX-AEX-HIC | Harvest adjusted to pH 4 | | 98 | 1089084 | 0.7 | |
| | Step 1: CEX Eluate | | 88 | 7397 | 147.2 | 0.2 |
| | Step 2: AEX flow-through | 95 | 91 | 542 | 13.7 | 0.3 |
| | Step 3: HIC Eluate | 71 | 83 | 19 | 28.9 | 0.0 |
| | Global process Yield | 58.2 | | | 58012 | |
| Process 2 | Harvest | | | 724905 | | |
| CEX-HIC-AEX | Harvest adjusted to pH 4 | | 98 | 1089084 | 0.7 | |
| | Step 1: CEX Eluate | | 88 | 7397 | 147.2 | 0.2 |
| | Step 2: HIC Eluate | 84 | | 2949 | 2.5 | 0.1 |
| | Step 3: AEX flow-through | 88 | 99 | 15 | 196.6 | 0.1 |
| | Global process Yield | 63.7 | | | 72615 | |

Figure 4:
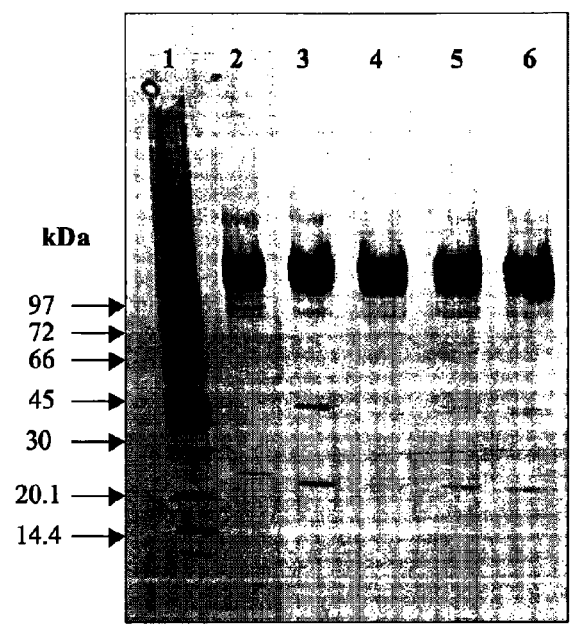
FIG. 4: shows a non-reduced silver stained SDS-PAGE—Steps 2 and 3 of the three step purification processes described in Examples 3 and 4.
  Lane 1—Molecular weight markers
  Lane 2—Standard anti-CD25 rhAb
  Lane 3—AEX Flow-through (step 2, Process 1)
  Lane 4—HIC Eluate (step 3, Bulk from Process 1)
  Lane 5—HIC Eluate (step 2, Process 2)
  Lane 6—AEX Flow-through (step 3, Bulk from Process 2)
Figure 5:
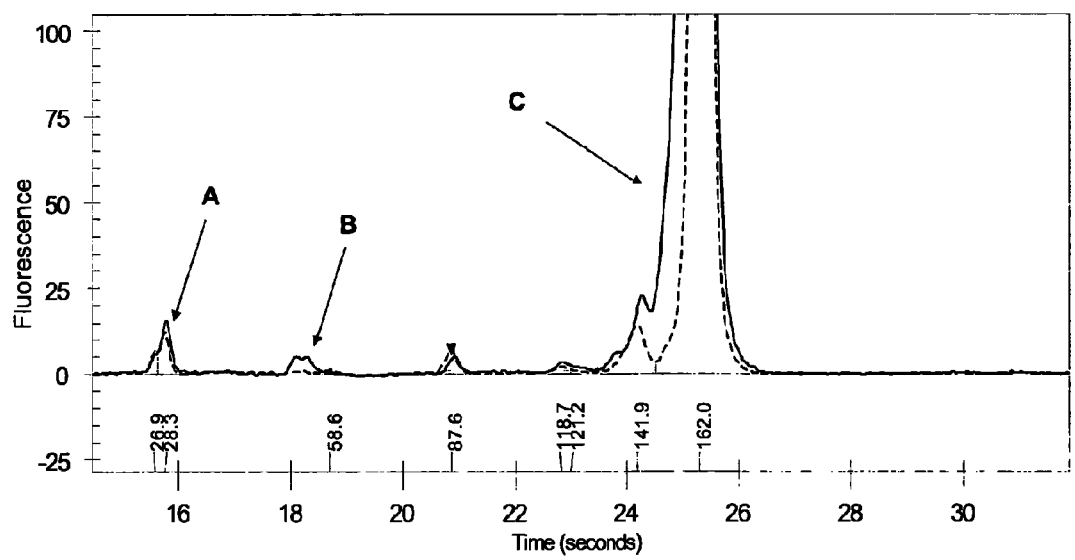
FIG. 5: LabChip 90 Electropherogram. Dotted line: Bulk from process1. Plain line: Bulk from process 2. A: light chain (~25 kDa), B: heavy chain (~50 kDa), C: anti-CD25 rhAb.

The global process yield as measured by OD at 280 nm is approximately 58% for process 1 and approximately 64% for process 2 (Table 3). In both cases less than 20 ppm of HCPs was obtained in the final bulk (Note: the value of HCPs of the capture eluate differs from the value in Table 2 as 2 different CEX eluates were mixed together). The final aggregate content for both processes is below 0.1%. FIG. 4 (SDS-PAGE analysis) shows that process 1 (Lane 4) gave a final bulk of a purity equivalent to the Ab standard (Lane 2) (presence of a band of very attenuated light chain). For process 2, bands representing the free light and free heavy chains were visible. These results were confirmed by the electopherogram in FIG. 5 (LabChip 90 analysis), where the main peak observed corresponds to the purified antibody. The product obtained by process 1 is free from free heavy chain (see peak B, dotted line). The values in Table 4 below confirm that the concentration of free heavy and free light chain are very low (<1%

TABLE 4

|  | Free Light chain (~25 kDa) | Free Heavy chain (~50 kDa) |
|---|---|---|
| Process 1 bulk | 0.7% | 0.1% |
| Process 2 bulk | 0.5% | 0.3% |

In addition, DNA levels in the purified bulk from process 1 (8.9 pg per mg of Ab) are equivalent to those obtained with the process Protein A affinity-CEX-AEX (9.4 pg per mg of Ab) (not shown).

Conclusion

The purity (HCPs, aggregates, incomplete antibody fragments, DNA) obtained in the purified bulk produced with process 1 consisting of the sequence CEX-AEX-HIC is equivalent to that of the process consisting of the sequence Protein A affinity-CEX-AEX.

OVERALL CONCLUSION

It has been shown that with the conditions developed for the capture step for antibodies on CEX, very low levels of HCPs (<10,000 ppm) and aggregates (<1%) could be obtained. Antibody fragments such as free heavy chain and free light chain were significantly reduced and undetectable by SDS-PAGE analysis.

This optimized capture step gives an antibody of high purity for HCPs, aggregates and antibody fragments at a high yield (>90%). In addition, the high dynamic capacity of the capture column when loading clarified harvest at pH4 (47 g/L) makes this step very cost-effective.

The three step process with the addition of an AEX and a HIC steps gives final material of purity comparable to a process with affinity chromatography on Protein A with respect to HCPs, aggregates, DNA and antibody fragments but at a lower cost (data not shown).

The three step process (according to either process1 or 2) resulted in highly purified anti-CD25 rhAb with an overall reduction of aggregates to less than 0.1%, overall reduction of HCPs to 15 to 20 ppm and an overall reduction of free light and heavy chains to less than 1%.

REFERENCES

1. Armour K L, Clark M R, Hadley A G, Williamson L M. (1999). Recombinant human IgG molecules lacking Fcgamma receptor I binding and monocyte triggering activities. Eur J. Immunol. 29(8):2613-24
2. Carter P J. (2006). Potent antibody therapeutics by design. Nat Rev Immunol. 2006 May; 6(5):343-57.
3. Follman D K, Fahrner R L. (2004). Factorial screening of antibody purification processes using three chromatography steps without protein A. J Chromatogr A. 2004 Jan. 23; 1024(1-2):79-85.
4. Grantham, R. (1974). Amino acid difference formula to help explain protein evolution. Science 185, 862-864.
5. Hinton P R, Johlfs M G, Xiong J M, Hanestad K, Ong K C, Bullock C, Keller S, Tang M T, Tso J Y, Vasquez M, Tsurushita N. (2004). Engineered human IgG antibodies with longer serum half-lives in primates. J Biol. Chem. 279(8): 6213-6.
6. Idusogie E E. et al. (2000). Mapping of the C1q binding site on rituxan, a chimeric antibody with a human IgG1 Fc. J. Immunol. 164(8):4178-84.
7. Idusogie E E. et al. (2001). Engineered antibodies with increased activity to recruit complement. J. Immunol. 166 (4):2571-5.
8. Kabat, E. A., Wu, T. T., Perry, H. M., Gottesman, K. S., and Foeller, C. (1991), Sequences of Proteins of Immunological Interest, 5th Ed., National Institutes of Health, Bethesda, Md.
9. Shields R L. et al. (2001). High resolution mapping of the binding site on human IgG1 for Fc gamma RI, Fc gamma RII, Fc gamma RIII, and FcRn and design of IgG1 variants with improved binding to the Fc gamma R. J Biol. Chem. 276(9):6591-604.
10. Steurer W, Nickerson P W, Steele A W, Steiger J, Zheng X X, Strom T B. (1995). Ex vivo coating of islet cell allografts with murine CTLA4/Fc promotes graft tolerance. J. Immunol. 155(3):1165-74
11. Vaccaro C, Zhou J, Ober R J, Ward E S. (2005). Engineering the Fc region of immunoglobulin G to modulate in vivo antibody levels. Nat. Biotechnol. 23(10):1283-8.
12. WO 02/094852
13. WO 03/102132A2
14. WO 2004/045512
15. WO 2005/001025
16. WO 92/13095
17. WO 97/13852
18. WO 98/23761

The invention claimed is:

1. A method separating and purifying an anti CD-25 antibody from a fluid comprising at least a cation exchange chromatography purification step comprising:
   (a) binding fluid comprising anti CD-25 antibody to a cation exchange resin;
   (b) washing the cation exchange resin with a buffer at a pH about 1 unit below the isoelectric point of the anti CD-25 antibody, the buffer having a conductivity of about 2 to 6 mS/cm; and
   (c) eluting the anti CD-25 antibody with a buffer at a pH about 1 unit below the isoelectric point of the anti CD-25 antibody with an increasing salt gradient;
   wherein:
   said anti CD-25 antibody comprises a human heavy chain variable region comprising the amino acid sequence as set forth in SEQ ID NO: 1 and a human kappa light chain variable region comprising the amino acid sequence as set forth in SEQ ID NO: 2, or conservative sequence modifications thereof; or
   said anti CD-25 antibody comprises the following VH CDRs: (i) SEQ ID NO: 3 (VH CDR1), SEQ ID NO: 4 (VH CDR2) and SEQ ID NO: 5 (VH CDR3) and the following VL CDRs: SEQ ID NO: 6 (VL CDR1), SEQ ID NO: 7 (VL CDR2) and SEQ ID NO: 8 (VL CDR3); or (ii) conservative sequence modifications of any one of the sequences defined in (i).

2. The method according to claim 1, wherein the method comprises subjecting the eluate of the cation exchange chromatography step to a further purification step selected from anion exchange chromatography or hydrophobic interaction chromatography.

3. The method according to claim 1, wherein the method comprises two additional purification steps on anion exchange chromatography and hydrophobic interaction chromatography, in either order.

4. The method according to claim 2, wherein the flow-through of the anion exchange chromatography is collected.

5. The method according to claim 1, wherein the binding of anti CD-25 antibody in step (a) is carried out at pH below 5.

6. The method according to claim 1, wherein the anti CD-25 antibody is diluted in water to a conductivity of less than 4 mS/cm at about pH 7.0 prior to its binding to the cation exchange resin in step (a).

7. The method according to claim 1, wherein the washing in step (b) is carried out at a pH from about 7 to about 8.5 at a conductivity of about 2 to 6 mS/cm.

8. The method according to claim 1, wherein the washing in step (b) is carried out with a phosphate buffer at about pH 8, having a conductivity of about 3.5 mS/cm.

9. The method according to claim 1, wherein the anti CD-25 antibody is eluted from the cation exchange resin with an increasing salt gradient at a conductivity ranging from about 2 to about 15 mS/cm at a pH of about 7 to about 8.5.

10. The method according to claim 1, wherein the anti CD-25 antibody is eluted from the cation exchange resin with an increasing NaCl gradient ranging from about 0 to about 150 mM at a pH ranging from about 7 to about pH 8.5.

11. The method according to claim 1, wherein cutting out the tail of the elution peak in step (c) is performed.

12. The method according to claim 1, wherein the cation exchange resin in step (a) is a strong cation exchange resin.

13. The method according to claim 12, wherein the strong cation exchange resin comprises sulfoethyl groups.

14. The method according to claim 12, wherein the resin is loaded at about pH 4, at a conductivity of about 15 mS/cm and at a dynamic capacity of about 40 to 47 g of anti CD-25 antibody per liter of packed cation exchange resin.

15. The method according to claim 1, wherein the eluate of the cation exchange resin resulting from step (c) has a Host Cell Protein ("HCP") level of less than 10,000 ppm or of less than 5,000 ppm.

16. The method according to claim 1, wherein the eluate of the cation exchange resin resulting from step (c) has an aggregate level of less than 1%.

17. The method according to claim 1, wherein the eluate of the cation exchange resin resulting from step (c) has levels of incomplete anti CD-25 antibody that are undetectable by SDS-PAGE under non-reducing conditions and silver staining when loading 1 mcg of anti CD-25 antibody.

18. The method according to claim 1, wherein the fluid comprising anti CD-25 antibody is clarified harvest.

19. The method according to claim 1, wherein the anti CD-25 antibody has an isoelectric point between about 7.5 and about 9.5.

20. The method according to claim 1, further comprising one or more step of ultrafiltration.

21. The method according to claim 1, further comprising formulating the purified anti CD-25 antibody into a pharmaceutical composition.

22. The method according to claim 1, wherein the anti CD-25 antibody has a human immunoglobulin constant region.

23. The method according to claim 22, wherein the immunoglobulin constant region is an $IgG_1$.

24. The method according to claim 22, wherein the constant region comprises a CH2 and a CH3 domain.

25. The method according to claim 22, wherein the constant region comprises a hinge, a CH2 and a CH3 domain.

26. The method according to claim 1, wherein the antibody is an anti CD-25 antibody comprising a human heavy chain variable region comprising the amino acid sequence as set forth in SEQ ID NO: 1 and a human kappa light chain variable region comprising the amino acid sequence as set forth in SEQ ID NO: 2, or conservative sequence modifications thereof.

27. The method according to claim 1, wherein the antibody is an anti CD-25 antibody comprising the following VH CDRs: (i) SEQ ID NO: 3 (VH CDR1), SEQ ID NO: 4 (VH CDR2) and SEQ ID NO: 5 (VH CDR3) and the following VL CDRs: SEQ ID NO: 6 (VL CDR1), SEQ ID NO: 7 (VL CDR2) and SEQ ID NO: 8 (VL CDR3): or (ii) conservative sequence modifications of any one of the sequences defined in (i).

28. The method according to claim 12, wherein said strong cation exchange resin comprises sulfonic acid groups.

29. The method according to claim 26, wherein the antibody is an anti CD-25 antibody comprising a human heavy chain variable region comprising the amino acid sequence as set forth in SEQ ID NO: 1 and a human kappa light chain variable region comprising the amino acid sequence as set forth in SEQ ID NO: 2.

30. The method according to claim 27, wherein the antibody is an anti CD-25 antibody comprising the following VH CDRs: (i) SEQ ID NO: 3 (VH CDR1), SEQ ID NO: 4 (VH CDR2) and SEQ ID NO: 5 (VH CDR3) and the following VL CDRs: SEQ ID NO: 6 (VL CDR1), SEQ ID NO: 7 (VL CDR2) and SEQ ID NO: 8 (VL CDR3).

* * * * *

UNITED STATES PATENT AND TRADEMARK OFFICE
CERTIFICATE OF CORRECTION

PATENT NO. : 8,168,185 B2
APPLICATION NO. : 12/521789
DATED : May 1, 2012
INVENTOR(S) : Alex Eon-Duval and Celine Teppet It is certified that error appears in the above-identified patent and that said Letters Patent is hereby corrected as shown below:

Column 4, Table 1,
Row "hIgG1e2", Column "Applications", "therapeutic us" should read --therapeutic use--.

Column 5, Table 1,
Row "hIgG1e3", Column "Mutations",
   "E233P/L234V/L235A/?G236 + A327G/A3305/P331S" should read
   --E233P/L234V/L235A/ΔG236 + A327G/A330S/P331S--.

Column 7,
Line 20, "protein with a with a buffer" should read --protein with a buffer--.

Column 10,
Line 56, "0.6% or less than 0.5% or less than 0.5% or" should read
   --0.6% or less than 0.5% or--.

Column 12,
Line 9, "through form the anion" should read --through from the anion--.
Line 12, "bstep" should read --b. step--.
Line 39, "(NHK)$_2$SO$_4$" should read --(NH$_4$)$_2$SO$_4$--.

Column 13,
Line 12, "or IgG." should read --or IgG$_4$.--.
Line 34, "or IgG." should read --or IgG$_4$.--.
Line 39, "Particularly It" should read --Particularly, it--.
Line 54, "b EU" should read --to EU--.
Line 59, "E233P/L234WL235A/?G236+ A327G/A330S/P331S" should read
   --E233P/L234V/L235A/ΔG236 + A327G/A330S/P331S--.
Line 61, "a EU" should read --at EU--.

Signed and Sealed this
Twenty-eighth Day of August, 2012

David J. Kappos
*Director of the United States Patent and Trademark Office*

CERTIFICATE OF CORRECTION (continued)
U.S. Pat. No. 8,168,185 B2

Column 14,
Line 32, "TAIL-R4," should read --TRAIL-R4,--.
Line 40, "IFNbeta" should read --IFN-beta--.

Column 16,
Line 59, "N or" should read --N- or--.
Line 61, "proteins and are" should read --proteins are--.

Column 18,
Line 34, "maybe" should read --may be--.
Line 53, "level are" should read --levels are--.
Line 55, "0.6% or less than 0.5% or less than 0.5% or" should read
    --0.6% or less than 0.5% or--.

Column 22,
Line 14, "at all time." should read --at all times.--.

Column 24,
Line 45, "flow through" should read --flow-through--.

Column 25,
Line 3, "at all time." should read --at all times.--.
Line 19, "aid buffer" should read --and buffer--.

SEQUENCE LISTING

```
<160> NUMBER OF SEQ ID NOS: 8

<210> SEQ ID NO 1
<211> LENGTH: 127
<212> TYPE: PRT
<213> ORGANISM: Homo sapiens

<400> SEQUENCE: 1

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg Tyr
```

```
                    20                  25                  30
Ile Ile Asn Trp Val Arg Gln Ala Pro Gly Gln Gly Leu Glu Trp Met
        35                  40                  45

Gly Arg Ile Ile Pro Ile Leu Gly Val Glu Asn Tyr Ala Gln Lys Phe
 50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Lys Asp Trp Phe Asp Tyr Trp Gly Gln Gly Thr Leu Val Thr
            100                 105                 110

Val Ser Ser Ala Ser Thr Lys Gly Pro Ser Val Phe Pro Leu Ala
            115                 120                 125

<210> SEQ ID NO 2
<211> LENGTH: 119
<212> TYPE: PRT
<213> ORGANISM: Homo sapiens

<400> SEQUENCE: 2

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Asp Arg Phe Ser Gly
 50                  55                  60

Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Tyr Gly Ser Ser Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro
            115

<210> SEQ ID NO 3
<211> LENGTH: 5
<212> TYPE: PRT
<213> ORGANISM: Homo sapiens

<400> SEQUENCE: 3

Arg Tyr Ile Ile Asn
 1               5

<210> SEQ ID NO 4
<211> LENGTH: 17
<212> TYPE: PRT
<213> ORGANISM: Homo sapiens

<400> SEQUENCE: 4

Arg Ile Ile Pro Ile Leu Gly Val Glu Asn Tyr Ala Gln Lys Phe Gln
 1               5                  10                  15

Gly

<210> SEQ ID NO 5
<211> LENGTH: 6
<212> TYPE: PRT
```

```
<213> ORGANISM: homo sapiens

<400> SEQUENCE: 5

Lys Asp Trp Phe Asp Tyr
1               5

<210> SEQ ID NO 6
<211> LENGTH: 11
<212> TYPE: PRT
<213> ORGANISM: homo sapiens

<400> SEQUENCE: 6

Arg Ala Ser Gln Ser Val Ser Ser Tyr Leu Ala
1               5                   10

<210> SEQ ID NO 7
<211> LENGTH: 7
<212> TYPE: PRT
<213> ORGANISM: homo sapiens

<400> SEQUENCE: 7

Gly Ala Ser Ser Arg Ala Thr
1               5

<210> SEQ ID NO 8
<211> LENGTH: 9
<212> TYPE: PRT
<213> ORGANISM: homo sapiens

<400> SEQUENCE: 8

Gln Gln Tyr Gly Ser Ser Pro Leu Thr
1               5
```